US007824694B2

(12) United States Patent
First et al.

(10) Patent No.: US 7,824,694 B2
(45) Date of Patent: Nov. 2, 2010

(54) METHODS FOR ENHANCING THERAPEUTIC EFFECTS OF A NEUROTOXIN

(75) Inventors: Eric R. First, Boston, MA (US); Ryan A. Irvine, Los Angeles, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 11/330,893

(22) Filed: Jan. 12, 2006

(65) Prior Publication Data

US 2007/0160633 A1 Jul. 12, 2007

(51) Int. Cl.
A61K 39/08 (2006.01)
A61K 35/30 (2006.01)
A61K 38/00 (2006.01)
(52) U.S. Cl. .................. 424/247.1; 424/239.1; 424/570; 514/2
(58) Field of Classification Search ........................ None
See application file for complete search history.

(56) References Cited

U.S. PATENT DOCUMENTS

| | | | | |
|---|---|---|---|---|
| 5,437,291 | A | 8/1995 | Pasricha et al. | 128/898 |
| 5,670,484 | A | 9/1997 | Binder | 514/14 |
| 5,714,468 | A | 2/1998 | Binder | 514/14 |
| 5,766,605 | A | 6/1998 | Sanders et al. | 424/239.1 |
| 5,989,545 | A | 11/1999 | Foster et al. | 424/183.1 |
| 6,063,768 | A | 5/2000 | First | 514/14 |
| 6,139,845 | A | 10/2000 | Donovan | 424/236.1 |
| 6,299,893 | B1 | 10/2001 | Schwartz et al. | 424/422 |
| 6,306,423 | B1 | 10/2001 | Donovan | 424/423 |
| 6,312,708 | B1 | 11/2001 | Donovan | 424/423 |
| 6,358,917 | B1 | 3/2002 | Carruthers et al. | 514/2 |
| 6,423,319 | B1 | 7/2002 | Brooks et al. | 424/239.1 |
| 6,429,189 | B1 * | 8/2002 | Borodic | 514/2 |
| 6,447,787 | B1 | 9/2002 | Gassner et al. | 424/247.1 |
| 6,458,365 | B1 | 10/2002 | Aoki et al. | 424/239.1 |
| 6,464,986 | B1 | 10/2002 | Aoki et al. | 424/239.1 |
| 6,503,884 | B1 * | 1/2003 | Ehrenberg et al. | 514/23 |
| 6,623,742 | B2 | 9/2003 | Voet | 424/236.1 |
| 6,787,517 | B1 * | 9/2004 | Gil et al. | 514/1 |
| 6,838,434 | B2 | 1/2005 | Voet | 514/2 |
| 6,869,610 | B2 * | 3/2005 | Aoki et al. | 424/239.1 |
| 2003/0224019 | A1 | 12/2003 | O'Brien | 424/239.1 |
| 2004/0009180 | A1 | 1/2004 | Donovan | 424/184.1 |
| 2004/0028706 | A1 | 2/2004 | Aoki et al. | 424/239.1 |
| 2004/0213811 | A1 | 10/2004 | Ackerman | 424/239.1 |
| 2005/0123567 | A1 | 6/2005 | First | 424/239.1 |
| 2005/0147625 | A1 | 7/2005 | First | 424/239.1 |
| 2005/0191320 | A1 | 9/2005 | Turkel et al. | |
| 2005/0191321 | A1 | 9/2005 | Turkel et al. | 424/239.1 |

FOREIGN PATENT DOCUMENTS

DE 101 50 415 A1 11/2001

WO WO 03/011333 7/2002

OTHER PUBLICATIONS

Silberstein et al., Headache 40: 445-450, 2000.*
Schulte-Mattler et al., Eur J Neurol. 13 Suppl 1:51-54, 2006.*
Schim., Curr Med Res and Opin 20: 49-53, 2004.*
Blumenfeld, Headache 42: 420, Abstract F20, 2002.*
Setler. Clin J Pain 18: S119-S124, 2002.*
Aurora, Exp Opin Pharmacother 7:1085-1095, 2006.*
Goadsby Exp Opin Emerging Drugs 11(3): 419-427, 2006.*
Elkind et al. J Pain 7: 688-696, 2006.*
Ferrante et al., Anesthesiology 103: 377-83, 2005.*
Shulte-Mattler et al. J Neurol Trans 115: 647-651, 2008.*
Jankovic J Neurol Neurosurg Psych 75: 951-957, 2004.*
Schulte-Mattler et al. Drug Dev Res 68: 397-402, 2007.*
U.S. Appl. No. 60/418,789, filed Oct. 15, 2002, Katz.
Aoki K., et al, *Mechanisms of the antinociceptive effect of subcutaneous Botox: Inhibition of peripheral and central nociceptive processing*, Cephalalgia Sep. 2003;23(7), p. 649.
Aoki, K., et al., *Botulinum toxin type A and other botulinum toxin serotypes: a comparative review of biochemical and pharmacological actions*, Eur J. Neurol 2001: (suppl 5), pp. 21-29.
Aoki, K., *Physiology and pharmacology of therapeutic botulinum neurotoxins*, in Kreyden, O., editor, Hyperhidrosis and botulinum toxin in dermatology, Basel, Karger; 2002; 30, pp. 107-116.
Bhattacharya K., et al., *Novel uses of botulinum toxin type A: two case reports*, Mov Disord 2000; 15(Suppl 2), pp. 51-52.
Bigalke H., et al., *Botulinum A Neurotoxin Inhibits Non-Cholinergic Synaptic Transmission in Mouse Spinal Cord Neurons in Culture*, Brain Research, 1985, 360, pp. 318-324.
Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol, 1981, 316, pp. 244-251.
Binz T. et al., *The Complete Sequence of Botulinum Neurotoxin Type A and Comparison with Other Clostridial Neurotoxins*, J Biological Chemistry; 1990 265(16), pp. 9153-9158.
Blugerman G., et al., *Multiple eccrine hidrocystomas: A new therapeutic option with botulinum toxin*, Dermatol Surg May 2003;29(5), pp. 557-559.
Borodic, et al., Eds. Jankovic J. et al., Therapy With Botulinum Toxin, Marcel Dekker, Inc., (1994), p. 150.
Boyd, *Mov Disord*,1995, 10(3):376.

(Continued)

*Primary Examiner*—Jeffrey Stucker
*Assistant Examiner*—Aditi Dutt
(74) *Attorney, Agent, or Firm*—Claude L. Nassif; Kenton Abel; Debra Condino

(57) ABSTRACT

The present invention relates to methods for enhancing the therapeutic effects of a neurotoxin, e.g., a *botulinum* toxin, where the methods comprise a "wash-down" (e.g., a decreased intake) of a current pain medication and an administration of a neurotoxin. In some embodiments, the present inventions relates to methods for enhancing the therapeutic effects of a neurotoxin for treating pain, e.g., headache pain.

36 Claims, 2 Drawing Sheets

OTHER PUBLICATIONS

Brem, H., et al, *Placebo-Controlled Trial of Safety and Efficacy of Intraoperative Controlled Delivery by Biodegradable Polymers of Chemotherapy for Recurrent Gliomas*, Lancet, 1995, 345, pp. 1008-1012.

Brin, M., et al., *Botulinum toxin type A: pharmacology*, in Mayer N., editor, Spasticity: etiology, evaluation, management and the role of botulinum toxin, 2002; pp. 110-124.

Bushara K., *Botulinum toxin and rhinorrhea*, Otolaryngol Head Neck Surg 1996;114(3), p. 507.

Coffield et al., Eds. Jankovic J. et al., *Therapy With Botulinum Toxin*, Marcel Dekker, Inc., (1994), Chapter 1.

Cui, M., et al., *Mechanisms of the antinociceptive effect of subcutaneous BOTOX® : inhibition of peripheral and central nociceptive processing*, Naunyn Schmiedebergs Arch Pharmacol 2002; 365 (supp 2): R17.

Dabrowski, et al, *Botulinum toxin as a novel treatment for self mutilation in Lesch-Nyhan syndrome*, Ann Neurol Sep. 2002;52(3 Suppl 1):S157.

Durham PL, Cady R, Blumenfled AJ. *Regulation of calcitonin generelated peptide secretion from trigeminal nerve cells by botulinum toxin type A: Implications for migraine therapy*. Headache; 2004, pp. 35-43.

Fung L. K. et al., *Pharmacokinetics of Interstitial Delivery of Carmustine 4-Hydroperoxycyclophosphamide and Paclitaxel From a Biodegradable Polymer Implant in the Monkey Brain*, Cancer Research 58:1998; pp. 672-684.

Gonelle-Gispert, et al., *Biochem J*, 1999, 1;339 (pt 1), pp. 159-165.

Habermann E., et al., *Tetanus Toxin and Botulinum A and C Neurotoxins Inhibit Noradrenaline Release From Cultured Mouse Brain*, J Neurochem 51(2):1988; pp. 522-527.

Habermann E., *Inhibition by Tetanus and Botulinum A Toxin of the release of [$^3$H ]Noradrenaline and [$^3$H ]GABA From Rat Brain Homogenate* Experientia 44:1988; pp. 224-226.

Habermann, *Naunyn-Schmiedeberg's Arch. Pharmacol.* 1974; 281, pp. 47-56.

*Harrison's Principles of Internal Medicine* (1998), edited by Anthony Fauci et al., 14$^{th}$ edition, published by McGraw Hill.

Heckmann M., et al., *Botulinum toxin type A injection in the treatment of lichen simplex: An open pilot study*, J Am Acad Dermatol Apr. 2002;46(4), pp. 617-9.

Jahanshahi M., et al., *Psychological functioning before and after treatment of torticollis with botulinum toxin*, J Neurol Neurosurg Psychiatry 1992; 55(3), pp. 229-231.

Jost W., *Ten years' experience with botulinum toxin in anal fissure*, Int J Colorectal Dis Sep. 2002;17(5), pp. 298-302.

Katsambas A., et al., *Cutaneous diseases of the foot: Unapproved treatments*, Clin Dermatol Nov.-Dec. 2002;20(6), pp. 689-699.

Li Y, et al., *Sensory and motor denervation influences epidermal thickness in rat foot glabrous skin*, Exp Neurol 1997;147, pp. 452-462.

Marjama-Lyons, J., et al., *Tremor-Predominant Parkinson's Disease*, Drugs & Aging 16(4):2000, pp. 273-278.

Moyer E et al., *Botulinum Toxin Type B: Experimental and Clinical Experience*, Chapter 6 of "Therapy With Botulinum Toxin", edited by Jankovic, J. et al. (1994), Marcel Dekker, Inc.

Murry T., et al., *Spasmodic dysphonia; emotional status and botulinum toxin treatment*, Arch Otolaryngol Mar. 1994; 120(3), pp. 310-316.

Naumann, Markus, et al., *Botulinum Toxin Type A in the Treatment of Focal, Axillary and Palmar Hyperhidrosis and Other Hyperhidrotic Conditions*, European J. Neurology 6 (Supp 4):1999, pp. S111-S115.

Pearce, L.B., *Pharmacologic Characterization of Botulinum Toxin For Basic Science and Medicine*, Toxicon 35(9); pp. 1373-1412, (1997).

Ragona, *The Laryngoscope* 109:1999, pp. 1344-1346.

Rogers J., et al., *Injections of botulinum toxin A in foot dystonia*, Neurology Apr. 1993;43(4 Suppl 2).

Sanchez-Prieto, J., et al., *Botulinum Toxin A Blocks Glutamate Exocytosis From Guinea Pig Cerebral Cortical Synaptosomes*, Eur J. Biochem 165:1987, pp. 675-681.

Schantz EJ, Johnson EA (1992) Properties and use of botulinum toxin and other microbial neurotoxins in medicine. Microbiol Rev 56, pp. 80-99.

Sevim, S., et al., *Botulinum toxin-A therapy for palmar and plantar hyperhidrosis*, Acta Neurol Belg Dec. 2002;102(4), pp. 167-170.

Sharma Sahshi K, Singh BR. *Enhancement of the endopepdidase activity of purified botulinum neurotoxins A and E by an isolated component of the native neurotoxin associated proteins*. Biochemistry: 2004, pp. 4791-4798.

Singh, *Critical Aspects of Bacterial Protein Toxins*, Chapter 4 of Natural Toxins II, edited by B.R. Singh et al., Plenum Press, New York (1996).

Sloop, *Neurology*, 48:1997, pp. 249-253.

Suputtitada, A., *Local botulinum toxin type A injections in the treatment of spastic toes*, Am J Phys Med Rehabil Oct. 2002;81(10), pp. 770-775.

Tacks, L., et al., *Idiopathic toe walking: Treatment with botulinum toxin A injection*, Dev Med Child Neurol 2002;44(Suppl 91):6.

Weigand et al, *Naunyn-Schmiedeberg's Arch. Pharmacol.* 1976; 292, pp. 161-165.

Woolf C. et al., *Neuropathic Pain: Aetiology, Symptoms, Mechanisms, and Management*, Lancet 1999; 353, pp. 1959-1964.

Schim, J., *Effect of Preventive Treatment with Botulinum Toxin Type A on Acute Headache Medication Usage in Migraine Patients*, Current Medical Research and Opinion, Hants, GB, Jan. 2004, vol. 20, No. 1, pp. 49-53.

Mennini, F.S., et al., *A one-year retrospective economic evaluation of botulinum toxin type A treatment of chronic tension headache*, Journal of Headache and Pain, 2004, Italy, vol. 5, No. 3, pp. 188-191.

Mathew, Ninan, T., et al., *Botulinum toxin type A: reduction in the use of acute pain medication in patients with transformed migraine* (TM), Cephalalgia, Scandinavian Press, vol. 25, No. 10, Oct. 2005, p. 993.

Relja, Maja, et al., *Botulinum toxin type-A reduces acute medication use in migraine patients*, Cephalalgia, vol. 23, No. 7, Sep. 2003, p. 699 (Abstract).

Argoff, C.E., *A focused review on the use of botulinum toxins for neuropathic pain*, Clinical Journal of Pain, 2002, vol. 18, No. 6, suppl. 6, pp. S177-S181.

* cited by examiner

FIG. 1

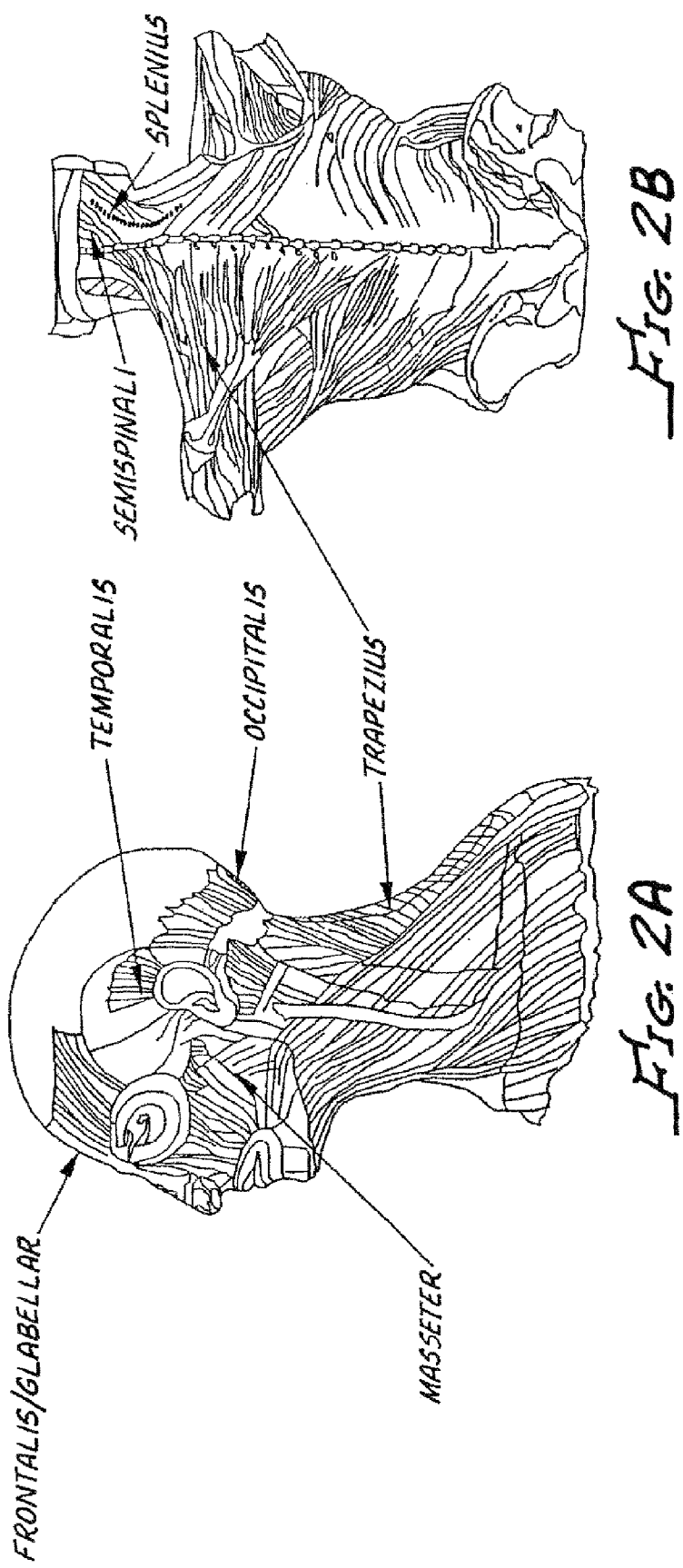

METHODS FOR ENHANCING THERAPEUTIC EFFECTS OF A NEUROTOXIN

BACKGROUND

The present invention relates to methods for enhancing the therapeutic effects of a neurotoxin, e.g., a *botulinum* toxin. In some embodiments, the present inventions relates to methods for enhancing the therapeutic effects of a neurotoxin for treating pain. In some embodiments, the present invention relates to methods for enhancing the therapeutic effects of a neurotoxin for treating pain caused by headaches and/or migraines, where the methods comprise a "wash-down" (e.g., a decreased intake) of a current pain medication and an administration of a neurotoxin. Optionally, the method comprises a "wash-up" (e.g., an increased intake) of the current pain medication after the administration of the neurotoxin.

The present discovery is surprising for at least the reason that it is known that after the administration of a neurotoxin to alleviate a pain, there is a lag time before the neurotoxin alleviates the pain. During this lag time, a medical practitioner would not prematurely decrease the amount of pain medication being used by a patient. Even more so, a medical practitioner would not prematurely decrease the amount of a pain medication being used by the patient prior to the patient being administered with a neurotoxin. In fact, there is a trend in the past few years that patients being treated for pain with a neurotoxin, e.g., a *botulinum* toxin, are allowed to take more pain medications concurrently with the administration of the neurotoxin. The present discovery is surprising because it comprises a step decreasing the intake of a pain medication prior the administration of a neurotoxin, or during the lag time.

Pain

Many, if not most ailments of the body cause pain. Generally pain is experienced when the free nerve endings which constitute the pain receptors in the skin as well as in certain internal tissues are subjected to mechanical, thermal, chemical or other noxious stimuli. The pain receptors can transmit signals along afferent neurons into the central nervous system and thence to the brain.

The causes of pain can include inflammation, injury, disease, muscle spasm and the onset of a neuropathic event or syndrome. Ineffectively treated pain can be devastating to the person experiencing it by limiting function, reducing mobility, complicating sleep, and dramatically interfering with the quality of life.

A muscle spasm can lead to stimulation of mechanosensitive pain receptors thereby causing a sensation of pain. Thus, pain can arise from or be due to a muscle spasm. Additionally, the spasm can indirectly stimulate the pain receptors by compressing onto blood vessels, causing ischemia in the tissue, which in turn releases pain inducing substances that stimulate pain receptors to cause pain sensations. Furthermore, a muscle spasm can cause a localized pH reduction which can be perceived as or which can engender pain signals. Hence, pain can be a secondary effect of a muscle spasm or muscle hypertonicity.

Inflammatory pain can occur when tissue is damaged, as can result from surgery or due to an adverse physical, chemical or thermal event or to infection by a biologic agent. When a tissue is damaged, a host of endogenous pain inducing substances, for example bradykinin and histamine can be released from the injured tissue. The pain inducing substances can bind to receptors on the sensory nerve terminals and thereby initiate afferent pain signals.

Additionally, pain inducing substances can be released from nociceptive afferent terminals, and neuropeptides released from sensory terminals can accentuate an inflammatory response. Thus, during inflammation there can be a sprouting of peptidergic peripheral fibers and an increased content of peptide, with many fibers showing a coexistence of substance P (SP) and calcitonin gene related peptide (CGRP). Substance P can induce contraction of endothelia cells, which in turn causes plasma extravasation to allow other substances (bradykinin, ATP, histamine) to gain access to the cite of injury and the afferent nerve terminals. Substance P release by the sensory nerve terminal can also degranulate mast cell. This process has been considered to be an important factor in neurogenic inflammation due to the release of inflammatory mediators such as histamine and serotonin and the release of proteolytic enzymes which catalyze the production of bradykinin. CGRP apparently does not produce plasma extravasation but is a powerful vasodilator and also act synergistically with SP and other inflammatory mediators to enhance plasma extravasation. All the above listed inflammatory mediators can either sensitize nociceptors or produce pain.

After activation of the primary sensory afferent neurons the next step in the transduction of sensory signals can be activation of projection neurons, which carry the signal, via the spinothalamic tract, to higher parts of the central nervous system such as the thalamic nuclei. The cell bodies of these neurons (other than those related to the cranial nerves) are located in the dorsal horn of the spinal cord. Here also one can find the synapses between the primary afferents and the projection neurons. The dorsal horn is organized into a series of laminae that are stacked, with lamina I being most dorsal followed by lamina II, etc. The different classes of primary afferents make synapses in different laminae. For cutaneous primary afferents, C-fibers make synapses in laminae I and II, A delta-fibers in laminae I, II and V, and A beta-fibers in laminae III, IV, and V. Deeper laminae (V-VII, X) are thought to be involved in the sensory pathways arriving from deeper tissues such as muscles and the viscera.

The predominant neurotransmitters at the synapses between primary afferent neurons and projection neurons are substance P, glutamate, CGRP and neuropeptide Y. The efficiency of transmission of these synapses can be altered via descending pathways and by local interneurons in the spinal cord. These modulatory neurons can release a number of mediators that are either inhibitory (e.g. opioid peptides, glycine) or excitatory (e.g. nitric oxide, cholecystokinin), to provide a mechanism for enhancing or reducing awareness of sensations.

Although inflammatory pain is generally reversible and subsides when the injured tissue has been repaired or the pain inducing stimulus removed, present methods for treating inflammatory pain have many drawbacks and deficiencies. Thus, the typical oral, parenteral or topical administration of an analgesic drug to treat the symptoms of pain or of, for example, an antibiotic to treat inflammatory pain causation factors can result in widespread systemic distribution of the drug and undesirable side effects. Additionally, current therapy for inflammatory pain suffers from short drug efficacy durations which necessitate frequent drug re-administration with possible resulting drug resistance, antibody development and/or drug dependence and addiction, all of which are unsatisfactory. Furthermore, frequent drug administration increases the expense of the regimen to the patient and can require the patient to remember to adhere to a dosing schedule.

Examples of treatments for inflammation and muscle pain include non-steroidal anti-inflammatory drugs (NSAIDS), including aspirin and ibuprofen; and opioids, such as morphine.

NSAIDs alleviate pain by inhibiting the production of prostaglandins released by damaged tissues. Prostaglandins have been shown to be peripheral mediators of pain and inflammation, as in arthritic diseases, and a reduction in their concentration provides relief to patients. It has been suggested that prostaglandins are involved in the mediation of pain in the spinal cord and the brain, which may explain the analgesic effects of NSAIDS in some pain states that do not involve inflammation or peripheral tissue damage. However, prostaglandins are only one of several mediators of pain. As such, NSAIDs have a ceiling of activity above which increasing doses do not give more pain relief. Furthermore, they have side effects that limit their usefulness. For example, NSAIDs can cause irritation of the gastrointestinal tract and prolonged use may lead to the development of extensive ulceration of the gut. This is particularly true in elderly patients who frequently use NSAIDs for their arthritis conditions.

The therapeutic actions of opioids are in the spinal cord. Opioids inhibit the efficiency of neurotransmission between the primary sensory afferents (principally C-fibers) and the projection neurons. They achieve this by causing a prolonged hyperpolarization of both elements of these synapses. The use of opioids is effective in alleviating most types of acute pain and chronic malignant pain. There are, however, a number of chronic malignant pain conditions which are partly or completely refractory to opioid analgesia, particularly those which involve nerve compression, e.g. by tumor formation. Unfortunately opioids also have unwanted side-effects including: (1) depression of the respiratory system, (2) constipation, and (3) psychoactive effects including sedation and euphoria. These side effects occur at doses similar to those that produce analgesia and therefore limit the doses that can be given to patients. Additionally, opioids such as morphine and heroin are well-known drugs of abuse that lead to physical dependence, which also involves the development of tolerance. With the development of tolerance, the dose of a drug required to produce the same analgesic effect increases with time. This may lead to a condition in which the doses required to alleviate the pain are life-threatening due to previously mentioned side-effects.

Although pain arising from inflammation and muscle spasm can be initiated by mechanical or chemical stimulation of the primary sensory neuron free terminal, neuropathic pain does not require an initial stimulus to the peripheral, free nerve terminal. Neuropathic pain is a persistent or chronic pain syndrome that can result from damage to the nervous system, the peripheral nerves, the dorsal root ganglion, dorsal root, or to the central nervous system.

Neuropathic pain syndromes include allodynia, various neuralgias such as post herpetic neuralgia and trigeminal neuralgia, phantom pain, and complex regional pain syndromes, such as reflex sympathetic dystrophy and causalgia. Causalgia is often characterized by spontaneous burning pain combined with hyperalgesia and allodynia.

Unfortunately, there is no existing method for adequately, predictably and specifically treating established neuropathic pain (Woolf C. et al., *Neuropathic Pain: Aetiology, Symptoms, Mechanisms, and Management*, Lancet 1999; 353: 1959-64) as present treatment methods for neuropathic pain consists of merely trying to help the patient cope through psychological or occupational therapy, rather than by reducing or eliminating the pain experienced.

For example, current methods to treat neuropathic pain include administration of local anesthetic blocks targeted to trigger points, peripheral nerves, plexi, dorsal roots, and to the sympathetic nervous system. However, these treatments have only short-lived antinociceptive effects. Additionally, longer lasting analgesic treatment methods, such as blocks by phenol injection or cryotherapy raise a considerable risk of irreversible functional impairment. Furthermore, chronic epidural or intrathecal (collectively "intraspinal") administration of drugs such as clonidine, steroids, opioids or midazolam have significant side effects and questionable efficacy.

Headache Pain

A headache is a pain in the head, such as in the scalp, face, forehead or neck. A headache can be a primary headache or a secondary headache. A primary headache is a headache which is not caused by another condition. Contrarily, a secondary headache is due to a disease or medical condition, such as an illness, infection, injury, stroke or other abnormality. Thus, with a secondary headache there is an underlying disorder that produces the headache as a symptom of that underlying disorder. Tension headache is the most common type of primary headache and tension headaches account for about 90% of all headaches. A tension headache is often experienced in the forehead, in the back of the head and neck, or in both regions. It has been described as a tight feeling, as if the head were in a vise. Soreness in the shoulders or neck is common. Nausea is uncommon with a tension headache.

Migraine headaches are recurrent headaches that may be unilateral or bilateral. Migraine headaches may occur with or without a prodrome. The aura of a migraine may consist of neurologic symptoms, such as dizziness, tinnitus, scotomas, photophobia, or visual scintillations (eg, bright zigzag lines). Migraines without aura are the most common, accounting for more than 80% of all migraines.

An estimated 10-20% of the population suffers from migraine headaches. An estimated 6% of men and 15-17% of women in the United States have migraine. Migraines most commonly are found in women, with a 3:1 female-to-male ratio.

About 2% of all headaches are secondary headaches. For example, a cervicogenic headache is a headache which is due to a neck problem, such as an abnormality of neck muscles, which can result from prolonged poor posture, arthritis, injuries of the upper spine, or from a cervical spine disorder. Sinus headache is another type of secondary headache. A sinus headache can be caused by inflammation and/or infection in the paranasal sinuses.

*Botulinum* Toxin

The genus *Clostridium* has more than one hundred and twenty seven species, grouped according to their morphology and functions. The anaerobic, gram positive bacterium *Clostridium botulinum* produces a potent polypeptide neurotoxin, *botulinum* toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The *botulinum* toxin can apparently pass unattenuated through the lining of the gut and attack peripheral motor neurons. Symptoms of *botulinum* toxin intoxication can progress from difficulty walking, swallowing, and speaking to paralysis of the respiratory muscles and death.

*Botulinum* toxin type A is the most lethal natural biological agent known to man. About 50 picograms of a commercially available *botulinum* toxin type A (purified neurotoxin complex)[1] is a $LD_{50}$ in mice (i.e. 1 unit). One unit of BOTOX® contains about 50 picograms (about 56 attomoles) of *botulinum* toxin type A complex. Interestingly, on a molar basis, *botulinum* toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63-84 (chapter 4) of Natural Toxins II, edited by B. R. Singh et al., Plenum Press, New York (1976) (where the stated $LD_{50}$ of *botulinum* toxin type A of 0.3 ng equals 1 U is corrected for the fact that about 0.05 ng of BOTOX® equals 1 unit). One unit (U) of *botulinum* toxin is defined as the $LD_{50}$ upon intraperitoneal injection into female Swiss Webster mice weighing 18 to 20 grams each.

*Available from Allergan, Inc., of Irvine, California under the tradename BOTOX® in 100 unit vials)

Seven, generally immunologically distinct *botulinum* neurotoxins have been characterized, these being respectively *botulinum* neurotoxin serotypes A, B, $C_1$, D, E, F and G each of which is distinguished by neutralization with type-specific antibodies. The different serotypes of *botulinum* toxin vary in the animal species that they affect and in the severity and duration of the paralysis they evoke. For example, it has been determined that *botulinum* toxin type A is 500 times more potent, as measured by the rate of paralysis produced in the rat, than is *botulinum* toxin type B. Additionally, *botulinum* toxin type B has been determined to be non-toxic in primates at a dose of 480 U/kg which is about 12 times the primate $LD_{50}$ for *botulinum* toxin type A. Moyer E et al., *Botulinum Toxin Type B: Experimental and Clinical Experience*, being chapter 6, pages 71-85 of "Therapy With *Botulinum* Toxin", edited by Jankovic, J. et al. (1994), Marcel Dekker, Inc. *Botulinum* toxin apparently binds with high affinity to cholinergic motor neurons, is translocated into the neuron and blocks the release of acetylcholine. Additional uptake can take place through low affinity receptors, as well as by phagocytosis and pinocytosis.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of *botulinum* toxin and for tetanus toxin. The carboxyl end segment of the H chain, $H_c$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of *botulinum* toxin activity appears to involve reduction of the disulfide bond joining the heavy chain, H chain, and the light chain, L chain. The entire toxic activity of *botulinum* and tetanus toxins is contained in the L chain of the holotoxin; the L chain is a zinc (Zn++) endopeptidase which selectively cleaves proteins essential for recognition and docking of neurotransmilter-containing vesicles with the cytoplasmic surface of the plasma membrane, and fusion of the vesicles with the plasma membrane. Tetanus neurotoxin, *botulinum* toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. *Botulinum* toxin serotype A and E cleave SNAP-25. *Botulinum* toxin serotype $C_1$ was originally thought to cleave only syntaxin, but was found to cleave syntaxin and SNAP-25. Each of the *botulinum* toxins specifically cleaves a different bond, except *botulinum* toxin type B (and tetanus toxin) which cleave the same bond. Each of these cleavages block the process of vesicle-membrane docking, thereby preventing exocytosis of vesicle content.

*Botulinum* toxins have been used in clinical settings for the treatment of neuromuscular disorders characterized by hyperactive skeletal muscles (i.e. motor disorders). In 1989 a *botulinum* toxin type A (Allergan, Inc., BOTOX®) complex was approved by the U.S. Food and Drug Administration for the treatment of blepharospasm, strabismus and VII nerve related disorder. Subsequently, in 2000, both a *botulinum* toxin type B (Elan, Inc., MYOBLOCTM™) and a *botulinum* toxin type A (Allergan, Inc., BOTOX®), were approved by the FDA for the treatment of cervical dystonia. Furthermore, a *botulinum* toxin type A (Allergan, Inc., BOTOX®), was FDA-approved for the treatment of glabellar lines in 2002 and for severe primary axillary hyperhidrosis in 2004. Non-type A *botulinum* toxin serotypes apparently have a lower potency and/or a shorter duration of activity as compared to *botulinum* toxin type A. Clinical effects of peripheral intramuscular *botulinum* toxin type A are usually seen within one week of injection. The typical duration of symptomatic relief from a single intramuscular injection of *botulinum* toxin type A averages about three months, although significantly longer periods of therapeutic activity have been reported. Although all the *botulinum* toxins serotypes apparently inhibit release of the neurotransmitter acetylcholine at the neuromuscular junction, they do so by affecting different neurosecretory proteins and/or cleaving these proteins at different sites. For example, *botulinum* types A and E both cleave the 25 kiloDalton (kD) synaptosomal associated protein (SNAP-25), but they target different amino acid sequences within this protein. *Botulinum* toxin types B, D, F and G act on vesicle-associated protein (VAMP, also called synaptobrevin), with each serotype cleaving the protein at a different site. Finally, *botulinum* toxin type $C_1$, has been shown to cleave both syntaxin and SNAP-25. These differences in mechanism of action may affect the relative potency and/or duration of action of the various *botulinum* toxin serotypes. Apparently, a substrate for a *botulinum* toxin can be found in a variety of different cell types. See e.g. *Biochem J* 1;339 (pt 1):159-65:1999, and *Mov Disord*, 10(3): 376:1995 (pancreatic islet B cells contains at least SNAP-25 and synaptobrevin).

The molecular weight of the *botulinum* neurotoxin component protein molecule, for all seven of the known *botulinum* toxin serotypes, is about 150 kD. Interestingly, the *botulinum* toxins are released by Clostridial bacterium as complexes, comprising the 150 kD *botulinum* toxin protein molecule along with associated non-toxin proteins. Thus, the

*botulinum* toxin type A complex can be produced by Clostridial bacterium as 900 kD, 500 kD and 300 kD forms. *Botulinum* toxin types B and $C_1$ are apparently produced as only a 700 kD or 500 kD complexes. *Botulinum* toxin type D is produced as both 300 kD and 500 kD complexes. Finally, *botulinum* toxin types E and F are produced as only approximately 300 kD complexes. The complexes (i.e. molecular weight greater than about 150 kD) are believed to contain various compositions of non-toxin hemaglutinin proteins and non-toxin and non-toxic nonhemaglutinin proteins; thus the variance in weights of the entire complexes. These non-toxin proteins (which along with the *botulinum* toxin molecule comprise the relevant neurotoxin complex) may act to provide stability against denaturation to the *botulinum* toxin molecule and protection against digestive acids when toxin is ingested (Sharma Sahshi K, Singh B. R. *Enhancement of the endopepdidase activity of purified botulinum neurotoxins A and E by an isolated component of the native neurotoxin associated proteins*. Biochemistry. pp 4791-4798: 2004. Additionally, it is possible that the larger (greater than about 150 kD molecular weight) *botulinum* toxin complexes may result in a slower rate of diffusion of the *botulinum* toxin away from a site of intramuscular injection of a *botulinum* toxin complex (Schantz E J, Johnson E A (1992) Properties and use of *botulinum* toxin and other microbial neurotoxins in medicine. Microbiol Rev_56_:80-99)$_{13}$ In vitro studies have indicated that *botulinum* toxin inhibits potassium cation induced release of both acetylcholine and norepinephrine from primary cell cultures of brainstem tissue. Additionally, it has been reported that *botulinum* toxin inhibits the evoked release of both glycine and glutamate in primary cultures of spinal cord neurons and that in brain synaptosome preparations *botulinum* toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain*, J Neurochem 51(2);522-527:1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165;675-681:1987. *Botulinum* toxn type A has also been shown to inhibit mediators (substance P, cGRP, and glutamate involved in pain and inflammation (Cui M, Aoki KR, *Mechanisms of the antinociceptive effect of subcutaneous* BOTOX): *Inhibition of peripheral and central nonciceptive processing*. Pain. 158-162; 2004; Durham PL, Cady R, Blumenfled AJ. *Regulation of calcitonin gene-related peptide secretion from trigeminal nerve cells by botulinum toxin type A: Implications for migraine therapy*. Headache. pp 35-43; 2004. Thus, when adequate concentrations are used, stimulus-evoked release of most neurotransmitters is blocked by *botulinum* toxin. See e.g. Pearce, L.B., *Pharmacologic Characterization of Botulinum Toxin For Basic Science and Medicine*, Toxicon 35(9); 1373-1412 at 1393; Bigalke H., et al., *Botulinum A Neurotoxin Inhibits Non-Cholinergic Synaptic Transmission in Mouse Spinal Cord Neurons in Culture*, Brain Research 360; 318-324:1985; Habermann E., *Inhibition by Tetanus and Botulinum A Toxin of the release of [³H]Noradrenaline and [³H]GABA From Rat Brain Homogenate*, Experientia 44;224-226:1988, Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316;244-251:1981, and; Jankovic J. et al., *Therapy With Botulinum Toxin, Marcel Dekker*, Inc., (1994), page 5.

*Botulinum* toxin type A can be obtained by establishing and growing cultures of *Clostridium botulinum* in a fermenter and then harvesting and purifying the fermented mixture in accordance with known procedures. All the *botulinum* toxin serotypes are initially synthesized as inactive single chain proteins which must be cleaved or nicked by proteases to become neuroactive. The bacterial strains that make *botulinum* toxin serotypes A and G possess endogenous proteases and serotypes A and G can therefore be recovered from bacterial cultures in predominantly their active form. In contrast, *botulinum* toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the *botulinum* toxin type B serotype only cleave a portion of the toxin produced. The exact proportion of nicked to unnicked molecules depends on the length of incubation and the temperature of the culture. Therefore, a certain percentage of any preparation of, for example, the *botulinum* toxin type B toxin is likely to be inactive, possibly accounting for the known significantly lower potency of *botulinum* toxin type B as compared to *botulinum* toxin type A. The presence of inactive *botulinum* toxin molecules in a clinical preparation will contribute to the overall protein load of the preparation, which has been linked to increased antigenicity, without contributing to its clinical efficacy. Additionally, it is known that *botulinum* toxin type B has, upon intramuscular injection, a shorter duration of activity and is also less potent than *botulinum* toxin type A at the same dose level.

High quality crystalline *botulinum* toxin type A can be produced from the Hall A strain of *Clostridium botulinum* with characteristics of $\geq 3 \times 10^7$ U/mg, an $A_{260}/A_{278}$ of less than 0.60 and a distinct pattern of banding on gel electrophoresis. The known Shantz process can be used to obtain crystalline *botulinum* toxin type A, as set forth in Shantz, E.J., et al, *Properties and use of Botulinum toxin and Other Microbial Neurotoxins in Medicine*, Microbiol Rev. 56;80-99:1992. Generally, the *botulinum* toxin type A complex can be isolated and purified from an anaerobic fermentation by cultivating *Clostridium botulinum* type A in a suitable medium. The known process can also be used, upon separation out of the non-toxin proteins, to obtain pure *botulinum* toxins, such as for example: purified *botulinum* toxin type A with an approximately 150 kD molecular weight with a specific potency of 1-2$\times 10^8$ LD$_{50}$ U/mg or greater; purified *botulinum* toxin type B with an approximately 156 kD molecular weight with a specific potency of 1-2$\times 10^8$ LD$_{50}$ U/mg or greater, and; purified *botulinum* toxin type F with an approximately 155 kD molecular weight with a specific potency of 1-2$\times 10^7$ LD$_{50}$ U/mg or greater.

*Botulinum* toxins and/or *botulinum* toxin complexes can be obtained from List Biological Laboratories, Inc., Campbell, California; the Centre for Applied Microbiology and Research, Porton Down, U.K.; Wako (Osaka, Japan), Metabiologics (Madison, Wisconsin) as well as from Sigma Chemicals of St Louis, Missouri. Pure *botulinum* toxin can also be used to prepare a pharmaceutical composition.

As with enzymes generally, the biological activities of the *botulinum* toxins (which are intracellular peptidases) is dependant, at least in part, upon their three dimensional conformation. Thus, *botulinum* toxin type A is detoxified by heat, various chemicals surface stretching and surface drying. Additionally, it is known that dilution of the toxin complex obtained by the known culturing, fermentation and purification to the much lower toxin concentrations used for pharmaceutical composition formulation, results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can stabilized with a stabilizing agent such as albumin and gelatin.

A commercially available *botulinum* toxin containing pharmaceutical composition is sold under the trademark BOTOX® (available from Allergan, Inc., of Irvine, California). BOTOX® consists of a purified *botulinum* toxin type A complex, albumin and sodium chloride packaged in sterile, vacuum-dried form. The *botulinum* toxin type A is made from a culture of the Hall strain of *Clostridium botulinum* grown in a medium containing N-Z amine and yeast extract. The *botulinum* toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks. *Neurology*, 48:249-53:1997.

It has been reported that *botulinum* toxin type A has been used in clinical settings as follows:

(1) about 75-125 units of BOTOX® per intramuscular injection (multiple muscles) to treat cervical dystonia;

(2) 5-10 units of BOTOX® per intramuscular injection to treat glabellar lines (brow furrows) (5 units injected intramuscularly into the procerus muscle and 10 units injected intramuscularly into each corrugator supercilii muscle);

(3) about 30-80 units of BOTOX® to treat constipation by intrasphincter injection of the puborectalis muscle;

(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:
(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

Additionally, intramuscular *botulinum* toxin has been used in the treatment of tremor in patients with Parkinson's disease, although it has been reported that results have not been impressive. Marjama-Jyons, J., et al., *Tremor-Predominant Parkinson's Disease*, Drugs & Aging 16(4);273-278:2000.

It is known that *botulinum* toxin type A can have an efficacy for up to 12 months (European J. *Neurology* 6 (Supp 4): S111-S1150:1999), and in some circumstances for as long as 27 months, when used to treat glands, such as in the treatment of hyperhydrosis. See e.g. Bushara K., *Botulinum toxin and rhinorrhea*, Otolaryngol Head Neck Surg 1996; 14(3):507, and *The Laryngoscope* 109:1344-1346:1999. However, the usual duration of an intramuscular injection of Botox® is typically about 3 to 4 months.

The success of *botulinum* toxin type A to treat a variety of clinical conditions has led to interest in other *botulinum* toxin serotypes. There are three commercially available *botulinum* type A preparations for use in humans: BOTOX®, available from Allergan, Inc., of Irvine, California; DYSPORT®, available from Beaufour Ipsen, Porton Down, England; and Xeomin®, available from Merz Pharmaceuticals GmbH, Frankfurt, Germany. A *Botulinum* toxin type B preparation (MYOBLOC®) is available from Elan Pharmaceuticals of San Francisco, California.

In addition to having pharmacologic actions at the peripheral location, *botulinum* toxins may also have inhibitory effects in the central nervous system. Work by Weigand et al, *Nauny-Schmiedeberg's Arch. Pharmacol.* 1976; 292,161-165, and Habermann, *Nauny-Schmiedeberg's Arch. PharmacoL* 1974; 281, 47-56 showed that *botulinum* toxin is able to ascend to the spinal area by retrograde transport. As such, a *botulinum* toxin injected at a peripheral location, for example intramuscularly, may be retrograde transported to the spinal cord.

U.S. Pat. No. 5,989,545 discloses that a modified clostridial neurotoxin or fragment thereof, preferably a *botulinum* toxin, chemically conjugated or recombinantly fused to a particular targeting moiety can be used to treat pain by administration of the agent to the spinal cord.

It has been reported that use of a *botulinum* toxin to treat various spasmodic muscle conditions can result in reduced depression and anxiety, as the muscle spasm is reduced. Murry T., et al., *Spasmodic dysphonia; emotional status and botulinum toxin treatment*, Arch Otolaryngol 1994 Mar; 120 (3): 310-316; Jahanshahi M., et al., *Psychological functioning before and after treatment of torticollis with botulinum toxin*, J Neurol Neurosurg Psychiatry 1992; 55(3): 229-231.

Additionally, German patent application DE 101 50 415 A1 discusses intramuscular injection of a *botulinum* toxin to treat depression and related affective disorders.

A *botulinum* toxin has also been proposed for or has been used to treat skin wounds (U.S. Pat. No. 6,447,787), various autonomic nerve dysfunctions (U.S. Pat. No. 5,766,605), tension headache, (U.S. Pat. No. 6,458,365), migraine headache pain (U.S. Pat. No. 5,714,468), sinus headache (U.S. patent application Ser. No. 429069), post-operative pain and visceral pain (U.S. Pat. No. 6,464,986), neuralgia pain (U.S. patent application Ser. No. 630,587), hair growth and hair retention (U.S. Pat. No. 6,299,893), dental related ailments (U.S. provisional patent application Ser. No. 60/418,789), fibromyalgia (U.S. Pat. No. 6,623,742), various skin disorders (U.S. patent application Ser. No. 10/731973), motion sickness (U.S. Pat. No. application Ser. No. 752,869), psoriasis and dermatitis (U.S. Pat. No. 5,670,484), injured muscles (U.S. Pat. No. 6,423,319) various cancers (U.S. Pat. No. 6,139,845), smooth muscle disorders (U.S. Pat. No. 5,437, 291), down turned mouth corners (U.S. Pat. No. 6,358,917), nerve entrapment syndromes (U.S. patent application 2003 0224019), various impulse disorders (U.S. patent application Ser. No. 423,380), acne (WO 03/011333) and neurogenic inflammation (U.S. Pat. No. 6,063,768). Controlled release toxin implants are known (see e.g. U.S. Pat. Nos. 6,306,423 and 6,312,708) as is transdermal *botulinum* toxin administration (U.S. patent application Ser. No. 10/194,805).

*Botulinum* toxin type A has been used to treat epilepsia partialis continua, a type of focal motor epilepsy. Bhattacharya K., et al., *Novel uses of botulinum toxin type A: two case reports*, Mov Disord 2000; 15(Suppl 2):51-52.

It is known that a *botulinum* toxin can be used to: weaken the chewing or biting muscle of the mouth so that self inflicted wounds and resulting ulcers can heal (Payne M., et al, *Botulinum toxin as a novel treatment for self mutilation in Lesch-Nyhan syndrome*, Ann Neurol 2002 Sep;52(3 Supp 1):S157); permit healing of benign cystic lesions or tumors (Blugerman G., et al., *Multiple eccrine hidrocystomas: A new therapeutic option with botulinum toxin*, Dermatol Surg 2003 May;29(5): 557-9); treat anal fissure (Jost W., *Ten years' experience with botulinum toxin in anal fissure*, Int J Colorectal Dis 2002 Sep;17(5):298-302, and; treat certain types of atopic dermatitis (Heckmann M., et al., *Botulinum toxin type A injection in the treatment of lichen simplex: An open pilot study*, J Am Acad Dermatol 2002 Apr;46(4):617-9).

Additionally, a *botulinum* toxin may have an effect to reduce induced inflammatory pain in a rat formalin model. Aoki K., et al, *Mechanisms of the antinociceptive effect of subcutaneous Botox: Inhibition of peripheral and central nociceptive processing*, Cephalalgia 2003 Sep;23(7):649. Furthermore, it has been reported that *botulinum* toxin nerve blockage can cause a reduction of epidermal thickness. Li Y, et al., *Sensory and motor denervation influences epidermal thickness in rat foot glabrous skin*, Exp Neurol 1997;147:452-462 (see page 459). Finally, it is known to administer a *botulinum* toxin to the foot to treat excessive foot sweating (Katsambas A., et al., *Cutaneous diseases of the foot: Unapproved treatments*, Clin Dermatol 2002 Nov-Dec;20(6):689-699; Sevim, S., et al., *Botulinum toxin-A therapy for palmar and plantar hyperhidrosis*, Acta Neurol Belg 2002 Dec;102(4): 167-70), spastic toes (Suputtitada, A., *Local botulinum toxin type A injections in the treatment of spastic toes*, Am J Phys Med Rehabil 2002 Oct;81(10):770-5), idiopathic toe walking (Tacks, L., et al., *Idiopathic toe walking: Treatment with botulinum toxin A injection*, Dev Med Child Neurol 2002;44 (Suppl 91):6), and foot dystonia (Rogers J., et al., *Injections of botulinum toxin A in foot dystonia*, Neurology 1993 Apr; 43(4 Suppl 2)).

Tetanus toxin, as wells as derivatives (i.e. with a non-native targeting moiety), fragments, hybrids and chimeras thereof can also have therapeutic utility. The tetanus toxin bears many similarities to the *botulinum* toxins. Thus, both the tetanus toxin and the *botulinum* toxins are polypeptides made by closely related species of *Clostridium* (*Clostridium tetani and Clostridium botulinum*, respectively). Additionally, both the tetanus toxin and the *botulinum* toxins are dichain proteins composed of a light chain (molecular weight about 50 kD) covalently bound by a single disulfide bond to a heavy chain (molecular weight about 100 kD). Hence, the molecular weight of tetanus toxin and of each of the seven *botulinum* toxins (non-complexed) is about 150 kD. Furthermore, for both the tetanus toxin and the *botulinum* toxins, the light chain bears the domain which exhibits intracellular biological (protease) activity, while the heavy chain comprises the receptor binding (immunogenic) and cell membrane translocational domains.

Further, both the tetanus toxin and the *botulinum* toxins exhibit a high, specific affinity for gangliocide receptors on the surface of presynaptic cholinergic neurons. Receptor mediated endocytosis of tetanus toxin by peripheral cholinergic neurons results in retrograde axonal transport, blocking of the release of inhibitory neurotransmitters from central synapses and a spastic paralysis. Contrarily, receptor mediated endocytosis of *botulinum* toxin by peripheral cholinergic neurons results in little if any retrograde transport, inhibition of acetylcholine exocytosis from the intoxicated peripheral motor neurons and a flaccid paralysis.

Finally, the tetanus toxin and the *botulinum* toxins resemble each other in both biosynthesis and molecular architecture. Thus, there is an overall 34% identity between the protein sequences of tetanus toxin and *botulinum* toxin type A, and a sequence identity as high as 62% for some functional domains. Binz T. et al., *The Complete Sequence of Botulinum Neurotoxin Type A and Comparison with Other Clostridial Neurotoxins*, J Biological Chemistry 265(16);9153-9158: 1990.

Acetylcholine

Typically only a single type of small molecule neurotransmitter is released by each type of neuron in the mammalian nervous system, although there is evidence which suggests that several neuromodulators can be released by the same neuron. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the bag 1 fibers of the muscle spindle fiber, by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. *Botulinum* toxin inhibits the release of both types of compounds from both types of cells in vitro, permeabilized (as by electroporation) or by direct injection of the toxin into the denervated cell. *Botulinum* toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

What is needed, therefore, is a method for enhancing the therapeutic use of neurotoxin, e.g., *botulinum* toxin, for treating various conditions, such as pain and headache pain.

SUMMARY

The present invention meets this need and provides methods for enhancing the therapeutic use of neurotoxin, e.g., *botulinum* toxin, for treating various conditions, such as pain and headache pain. The therapeutic effect of the neurotoxin is enhanced by, for example, being administered at a lower dose/frequency but still achieving the same or better therapeutic end result.

In some embodiments, the methods of the present invention comprise the steps of decreasing a dose of at least one current headache medication that is being used by the patient to a lower dose ("wash-down"), and locally administering a neurotoxin to the patient.

In some embodiments, the wash-down may be prior to the step of administering the neurotoxin. Further, the wash-down period may occur within about an amount of time equal to that required to achieve the current dose relative to the lower dose. In some embodiments, the amount of time required to achieve the current dose is provided by a product instruction insert of the medication.

In some embodiments, the wash-down is to reduce the pain medication in the blood circulation of the patient to about 5% (or more) of the original level prior to wash-down. In some embodiments, the wash-down is to reduce the pain medication in the blood circulation of the patient to about 10% (or more) of the level prior to wash-down. In some embodiments, the wash-down is to reduce the pain medication in the blood circulation of the patient to about 25% (or more) of the level prior to wash-down. In some embodiments, the wash-down is to reduce the pain medication in the blood circulation of the patient to about 50% (or more) of the level prior to wash-down.

For patients who are on prophylactic pain medications, the wash-down step of the prophylactic pain medication is such that there is still residual prophylactic pain medication in the patient's circulatory system. For example, in some embodiments, the wash-down is to reduce the prophylactic pain medication in the blood circulation of the patient to about 5% (or more) of the original level prior to wash-down. In some embodiments, the wash-down is to reduce the prophylactic pain medication in the blood circulation of the patient to about 10% (or more) of the level prior to wash-down. In some embodiments, the wash-down is to reduce the prophylactic pain medication in the blood circulation of the patient to about 25% (or more) of the level prior to wash-down. In some embodiments, the wash-down is to reduce the prophylactic pain medication in the blood circulation of the patient to about 50% (or. more) of the level prior to wash-down.

After the administration of the neurotoxin, the methods comprise an optional step of increasing the dose of the lowered headache dose.

The term "neurotoxin" employed herein refers to one or more of a toxin made by a bacterium, for example, a *Clostridium botulinum, Clostridium butyricum, Clostridium beratti, Clostridium tetani*. In some embodiments, the neurotoxin is a *botulinum* toxin. The *botulinum* toxin may be a *botulinum* toxin type A, type B, type $C_1$, type D, type E, type F, or type G. In some embodiments, the neurotoxin is a *botulinum* toxin type A. Unless stated otherwise, the dose of the neurotoxin referenced herein is equivalent to that of a *botulinum* toxin type A. The assays required to determine equivalency to the therapeutic effectiveness of *botulinum* toxin type A at a certain dosage are well established.

Further, the following definitions apply herein:

"About" means approximately or nearly and in the context of a numerical value or range set forth herein means ±10% of the numerical value or range recited or claimed.

"Alleviating" means a reduction in the occurrence of a pain, of a headache.or of a symptom. Thus, alleviating includes some reduction, significant reduction, near total reduction, and total reduction. An alleviating effect may not appear clinically for between 1 to 7 days after administration of a Clostridial toxin to a patient.

"*Botulinum* toxin" means a *botulinum* neurotoxin as either pure toxin or complex, and excludes *botulinum* toxins which are not neurotoxins such as the cytotoxic *botulinum* toxins $C_2$ and $C_3$.

"Local administration" means administration (i.e. by a subcutaneous, intramuscular, subdermal or transdermal route) of a pharmaceutical agent to or to the vicinity of a muscle or of a subdermal location or in the head of a patient by a non-systemic route. Thus, local administration excludes systemic (i.e. to the blood circulation system) routes of administration, such as intravenous or oral administration. Peripheral administration means administration to the periphery (i.e. to a location on or within a limb, trunk or head of a patient) as opposed to a visceral or gut (i.e. to the viscera) administration.

"Treating" means to alleviate (or to eliminate) at least one symptom of pain (such as a headache pain), either temporarily or permanently.

DRAWINGS

The following drawings are presented to assist understanding of aspects and features of the present invention.

Figure 1:
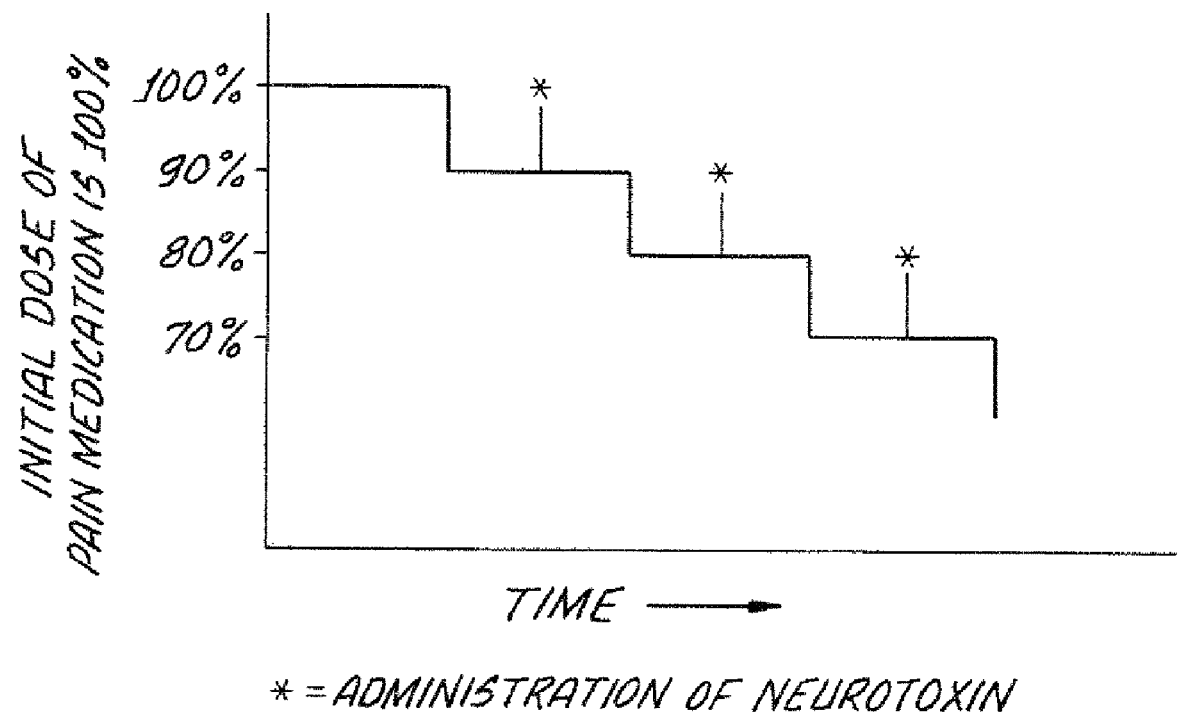

FIG. 1 shows an exemplary scheme for a stepwise wash-down.

FIG. 2A comprises, a left side diagrammatic view of human muscle anatomy from the shoulders up, and FIG. 2B comprises a diagrammatic view of the back or trunk (including the neck), both views showing the anatomy and placement of the muscles with the overlying skin removed and sites to inject for treatments 1, 2, 3 and 4, as described herein.

DESCRIPTION

The present invention is based, in part, upon the discovery that a reduction in the administration of a pain medication prior to the administration of a neurotoxin, or prior to the therapeutic onset of the neurotoxin after its administration, can enhance the therapeutic effects of the neurotoxin. The therapeutic effect of the neurotoxin is enhanced by, for example, being administered at a lower dose/frequency but still achieving the same or better therapeutic end result.

As stated above, the term "neurotoxin" refers to one or more of a toxin made by a bacterium, for example, a *Clostridium botulinum, Clostridium butyricum, Clostridium beratti, Clostridium tetani*. In some embodiments, the neurotoxin is a *botulinum* toxin. The *botulinum* toxin may be a *botulinum* toxin type A, type B, type $C_1$, type D, type E, type F, or type G. In some embodiments, the neurotoxin is a *botulinum* toxin type A. Unless stated otherwise, the dose of the neurotoxin referenced herein is equivalent to that of a *botulinum* toxin type A. In some embodiments, the neurotoxin dose suitable for the present invention may be from about 1 Units to about 1,000 Units (in terms of unit equivalency to *botulinum* toxin type A).

In some embodiments, the methods of the present invention can enhance the therapeutic effects of a neurotoxin for its use in preventing and/or treating a headache pain. The methods comprise the steps of decreasing at least one current dose of a headache medication being used by the patient to a lower dose ("wash-down"), and locally administering a neurotoxin to the patient.

The wash-down may be prior to the step of administering the neurotoxin. In some embodiments, the wash-down occurs within about an amount of time equal to that required to achieve the current dose relative to the lower dose. In some embodiments, the amount of time required to achieve the current dose is provided by a product instruction insert of the medication. Further, the wash-down step may involve decreasing the current dose via a titration process. In some embodiments, the titration process is in reverse of a dosing regimen used by the patient to achieve the current dose.

In some embodiments, the titration process is in reverse of a dosing regimen provided by a product instruction insert of the medication to achieve the current dose. For example, the titration schedule as provided by the product insert for topiramate is 25-50 mg nightly for one week. Subsequently, at weekly intervals, the dose is increased by 25-50 mg/day and taken in two divided doses. The reverse of this titration process would be, at weekly intervals, reduction of 25-50 mg/day, until the initial dose (25-50 mg/day) is reached.

In some embodiments, the wash-down occurs within about an amount of time equal to about 1 to 5 times a half-life of the medication. For example, the wash-down may occur within about an amount of time equal to 2 times a half-life of the medication, 2.5 times a half-life of the medication, or 3 times a half-life of the medication. In some embodiments, the wash-down occurs within about an amount of time equal to about 2 hours to 6 weeks.

The lower dose with reference to the wash-down may be the initial dose or a factor of the minimum effective dose (dose at which the patient first reported effectiveness) of the medication. For example, the lower dose may be about 0.10 to about 0.90 that of a minimum effective dose. In some embodiments, the lower dose may be about 0.10 to about 0.80, or about 0.10 to about 0.30, that of a minimum effective dose. In some embodiments, the lower dose may be about 0.75 that of a minimum effective dose.

In some embodiments, the wash-down step is to achieve a plasma level of less than 75% of the headache medication being washed-down, prior to the administration of a neurotoxin. In some embodiments, the wash-down step is to achieve a plasma level of less than 50% of the headache medication being washed-down. In some embodiments, the wash-down step is to achieve a plasma level of less than 25% of the headache medication being washed-down.

Although plasma level of a headache medication may be useful in determining the appropriate time at which to administer a neurotoxin, it is also possible to wash-down the pain medication only to a level that may be tolerated by the patient, and then administer the neurotoxin. For example, a method in accordance with the present invention comprises lowering the dose of the pain medication (wash-down) to a level where the patient would be able to tolerate a headache pain, and then administering a neurotoxin.

Although the wash-down step can be practiced prior to the administration of a neurotoxin, in some embodiments, the wash-down step may begin at or after the step of administration of a neurotoxin. In some embodiments, the wash-down step may be prior to the onset of the therapeutic effect of the neurotoxin. The onset of the therapeutic affect of the neurotoxin may be determined by an improvement of a diseased condition by about 1% to about 25%. For example, an onset of the therapeutic affect of the neurotoxin for the treatment of a headache pain may be determined by a reduction of the pain by about 1% to about 25%.

In some embodiments, the wash-down may be proceeded via a stepwise process. For example, there are situations where a reduction to a particular pain medication dose is not immediately achievable because the patient is not able to tolerate the pain at that particular lower dose. An application of a stepwise wash-down may be effective in a situation like this. A stepwise wash-down comprises a wash-down and an administration of a neurotoxin in alternation, for as many times as needed. For example, a stepwise wash-down in accordance with the present invention comprises the following steps in order:
(1) decreasing a dose of a pain medication by 10%,
(2) administering a neurotoxin,
(3) decreasing the dose of the pain medication by another 10%,
(4) administering the neurotoxin, etc.

FIG. 1 shows an exemplary scheme for a stepwise wash-down. Since the stepwise wash-down allows for a smaller reduction in the dose of the pain medication, it may be more appropriate for some patients. Further, as the dose of the pain medication is sequentially decreased, the dose of the neurotoxin administration may also sequentially decrease.

In some embodiments, the wash-down step comprises decreasing the dose of all the pain medications that the patient is currently taking. In some embodiments, the wash-down step comprises decreasing the dose of only some of the pain medications.

In some embodiments, the wash-down step comprises decreasing the dose of only the prophylactic pain medication, and still allowing the patient to continue with the acute pain medication at full dose. In some embodiments, the wash-down step comprises decreasing the dose of only the acute pain medication, and allowing the patient to continue with the prophylactic pain medication at full dose. In some embodiments, the wash-down step comprises decreasing the dose of both the prophylactic and the acute pain medications.

The current pain medication that may be washed-down in accordance with the present invention include a prophylactic headache medication and/or an acute pain medication. In some embodiments, only the prophylactic pain medication is washed-down. In some embodiments, only the prophylactic pain medication is washed-down.

Medications that may be used as a prophylactic or acute headache medication include a beta-blocker, anti-epileptic agent, calcium channel blocker, sodium channel blocker, chloride enhancing agent, serotonin antagonists, selective serotonin re-uptake inhibitor, amitriptyline, tricyclic anti-depressant, valproic acid and derivatives, nonsteroidal anti-inflammatory drug and combinations thereof.

In some embodiments, a calcium channel blocker selected from the group consisting of topiramate, gabapentin, levetiracetam, zonisamide, ethosuximide, lamotrigine, oxcarbazepine, pregabalin and combinations thereof. In some embodiments, a sodium channel blocker selected from the group consisting of topiramate, carbamazepine, oxcarbazepine, phenytoin, valproate, lamotrigine and combinations thereof. In some embodiments, a chloride-enhancing agent selected from the group consisting of gabapentin, levetiracetam and tiagabine. In some embodiments, the current headache medication is a aspirin (acetylsalicylic acid) or acetaminophen.

The methods of the present invention are effective in treating pain arising from a tension headache, a migraine headache, a cluster headache and/or a sinus headache. Further, the methods of the present invention are effective in treating pain arising from a chronic headache, an episodic headache and/or an acute headache.

In preventing or treating a headache pain in a patient in need thereof, the neurotoxin may be locally administered to a head muscle, face muscle, an upper neck muscle, or a combination thereof. More specifically, the neurotoxin may be administered locally to a frontalis muscle, a glabellar muscle, a masseter muscle, a temporalis muscle, a occipitalis muscle, a trapezius muscle, a semispinali muscle, a splenius muscle, a corrugator muscle, a procerus muscle, or a combination thereof.

According to our invention, the neurotoxin (such as *botulinum toxin* serotype A, B, $C_1$, D, E, F or G) can be injected locally (e.g. intramuscular injection) into or in the vicinity where a patient is experiencing the pain to thereby suppress the pain or prevent its occurrence. In some embodiments, the neurotoxin can be administered intradermally and/or subdermally. Further, the neurotoxin can be administered at one or multiple sites. Table 1 and FIGS. 2A and 2B show an exemplary injection scheme of a neurotoxin (e.g. *botulinum toxin*) in accordance with the present invention.

TABLE 1

| Muscle Area | Number of Neurotoxin Units[a] | Bilateral Injection | Total Dose (U) |
| --- | --- | --- | --- |
| Frontal/Glabellar | 25-40 | No | 25-40 |
| Occipitalis | 10 | Yes | 20 |
| Temporalis | 10-25 | Yes | 20-50 |
| Masseter (optional) | 0-25 | Yes | 0-50 |
| Trapezius | 10-30 | Yes | 20-60 |
| Semispinalis | 5-10 | Yes | 10-20 |
| Splenius capitis | 5-10 | Yes | 10-20 |
| Total Dose Range | | | 105-260 |

In some embodiments, the methods of the present invention reduces the frequency of the headache pain by more than about 10% to about 95% as compared to the frequency and/or intensity of headache pain treated with a neurotoxin that is not accompanied by a wash-down. For example, patients being treated with methods of the present invention would experience more than 15, preferably more than 20, headache-free days out of 30 days. In some embodiments, the therapeutic effects provided by the neurotoxin can persist for a relatively long period of time, for example, for more than two months, and potentially for several years.

In some embodiments, the methods of the present invention reduces the intensity of the headache pain by more than about 10% to about 95% as compared to the intensity of headache treated with a neurotoxin that is not accompanied by a wash-down.

After the wash-down and administration of the neurotoxin, the 20 methods of the present invention optionally comprise the step of increasing the lower dose of the headache medication ("wash-up"). In some embodiments, the wash-up occurs at about when the neurotoxin begins to alleviate the pain. For example, the wash-up can occurs at about 5 to 14 days after the administration of the neurotoxin. In some embodiments, the wash-up further decreases the frequency and/or intensity of the headache pain.

For patients who are concurrently using a pain medication, and who are also being administered a neurotoxin for the treatment of conditions other than headache pain, the wash-down step of the present invention would also be effective to enhance the therapeutic effects of the neurotoxin in treating those conditions. For example, patients who are concurrently using a pain medication, and are being administered a neurotoxin for the treatment of a neuromuscular disorder, an autonomic nervous system disorder and/or non-headache pain may also benefit from the present invention.

In some embodiments, the method for treating a neuromuscular disorder, autonomic disorder and/or non-headache pain comprises a wash-down step. The wash-down may be prior to the administration of a neurotoxin or prior to the onset of the therapeutic effect of the neurotoxin.

The neuromuscular disorders and conditions that may be treated with the present method include: for example, strabismus, blepharospasm, spasmodic torticollis (cervical dystonia), oromandibular dystonia and spasmodic dysphonia (laryngeal dystonia). Muscle spasm conditions that may be treated with the present method include those arising from: post-stroke spasticity, cerebral palsy, spinal cord injury, brain injury, and multiple sclerosis. Autonomic nervous system disorders may also be treated with the present methods include: glandular malfunctioning (e.g., excessive sweating and excessive salivation) and respiratory malfunctioning (chronic obstructive pulmonary disease and asthma). Non-headache pain that may be treated with the present methods include: pain caused by muscle tension, or spasm, or pain that is not associated with muscle spasm; articular and non-articular pain arising from a joint; including; rheumatoid arthritis, acute crystal-induced arthritis, refractory sacroiliac joint pain related to ankylosing spondylitis or other spondyloarthropathies, juvenile rheumatoid arthritis, osteoarthritis, rotator cuff tendinitis, frozen shoulder, and other causes of shoulder pain, lateral epicondylitis (tennis elbow), femoral trochanteric pain syndromes (ie, bursitis), and periarticular knee pain including; anserine bursitis, synovial plicas, bone pain, in particular, metastatic bone cancer pain; neuropathic pain (e.g., post-herpetic pain), peripheral neuropathy (e.g. diabetic peripheral neuropathy), de Quervain's tenosynovitis, plantar fasciitis, carpal tunnel syndrome, tarsal tunnel syndrome, phantom pain and myofascial pain. With regards to pain that is not associated with muscle spasm, Foster et al. in U.S. Pat. No. 5,989,545 discloses that a *botulinum* toxin conjugated with a targeting moiety may be administered centrally (intrathecally) to alleviate pain. The disclosure of Foster et al. is incorporated in its entirety by reference herein.

In some embodiments, the present invention excludes the treatment of myofascial pain. In some embodiments, the present invention includes the treatment of myofascial pain, with a proviso that the wash-down of the pain medication is at the most 13 days prior to the injection of the neurotoxin. It is surprisingly discovered that a wash-down period of 13 days or less will allow for an effective treatment of myofascial pain. In some embodiments, the methods for reducing myofascial pain includes a wash-up.

In some embodiments, the method for treating a smooth muscle disorder, glandular disorder and/or non-headache pain comprises a wash-down step. The wash-down may be prior to the administration of a neurotoxin or prior to the onset of the therapeutic effect of the neurotoxin.

The smooth muscle disorders and conditions that may be treated with the present method include: for example, interstitial cystitis, detrusor external sphincter dyssynergia, overactive bladder, (neurogenic incontinence) detrusor hyperreflexia; detrusor sphincter dyssynergia and urinary retention, non-neurogenic bladder conditions and other bladder and urethral conditions such as; idiopathic conditions of hyper-contraction of the urethral sphincter or for cases in which lowering urethral resistance may improve voiding function (eg, bladder hypocontractility). The glandular disorders that may be treated with the present method include: for example; benign prostatic hypertrophy.

With respect to applying the present methods for treating pain in general, our invention is preferably practiced by administering a *botulinum* toxin directly to a location where a patient is or is predisposed to experience pain. Without wishing to be bound by theory a physiological mechanism can be proposed for the efficacy of the present invention. It is known that muscles have a complex system of innervation and sensory output. Thus, anterior motor neurons located in each segment of the anterior horns of the spinal cord gray matter give rise to efferent alpha motor neurons and efferent gamma motor neurons that leave the spinal cord by way of the anterior roots to innervate skeletal (extrafusal) muscle fibers. The alpha motor neurons cause contraction of extrafusal skeletal muscle fibers while the gamma motor neurons innervate the intrafusal fibers of skeletal muscle. As well as excitation by these two type of efferent anterior motor neuron projections, there are additional, afferent sensory neurons which project from muscle spindle and golgi tendon organs and act to transmit information regarding various muscle parameter status to the spinal cord, cerebellum and cerebral cortex. These afferent motor neurons which relay sensory information from the muscle spindle include type Ia and type II sensory afferent neurons. See e.g. pages 686-688 of Guyton A.C. et al., *Textbook of Medical Physiology*, W.B. Saunders Company 1996, ninth edition.

Significantly, it has been determined that a neurotoxin, i.e., a *botulinum* toxin, can act to reduce transmission of sensory information from muscle type Ia afferent neurons. Aoki, K., *Physiology and pharmacology of therapeutic botulinum neurotoxins*, in Kreyden, O., editor, Hyperhidrosis and *botulinum* toxin in dermatology, Basel, Karger; 2002; 30: pages 107-116, at 109-110. And it has been hypothesized that *botulinum* toxin can have a direct effect upon muscle cell sensory afferents and modify signals from these afferents to the central nervous system. See e.g. Brin, M., et al., *Botulinum toxin type A: pharmacology*, in Mayer N., editor, Spasticity: etiology, evaluation, management and the role of *botulinum* toxin, 2002; pages 110-124, at 112-113; Cui, M., et al., *Mechanisms of the antinociceptive effect of subcutaneous BOTOX®. inhibition of peripheral and central nociceptive processing*, Naunyn Schmiedebergs Arch Pharmacol 2002; 365 (supp 2): R17; Aoki, K., et al., *Botulinum toxin type A and other botulinum toxin serotypes: a comparative review of biochemical and pharmacological actions*, Eur J. Neurol 2001: (suppl 5); 21-29. Thus, it has been demonstrated that *botulinum* toxin can cause an altered sensory output from muscle to CNS and brain.

Importantly, the sensory neurons from which afferent output is to be inhibited by a method according to the present invention need not be located on or within a muscle, but can be in an intradermal or subdermal location.

Thus, pain can be due to sensory input from afferent facial area neurons. Administration of a *botulinum* toxin to a facial muscles or skin to reduce sensory output from the muscle can result in alleviation of and prevention of pain.

It is our hypothesis, as may be the case in the treatment of a migraine headache with a neurotoxin, that signals transmitted by afferent pain nerves in or on muscle tissue (i.e. muscle spiridle fibers and muscle pain fibers) or as a part of sensory structures in the skin or subdermally induce the pain sensation. That is, afferent signal from muscles or skin structures provide sensory information to the brain which then leads to the generation of pain. Thus, a local administration of a neurotoxin, e.g., a *botulinum* toxin, to muscle spindle fibers, pain fibers or other sensors in or in the vicinity of a muscle can act to alter the neural signal afferent output from these muscles to the brain and thereby decrease the sensation of pain.

Important elements of our invention are firstly that is practiced by use of a local administration of low dose of a neurotoxin, e.g., a *botulinum* toxin. The selected low dose may not cause a muscle paralysis. Secondly, the invention can be practiced by local administration of the low dose of the *botulinum* toxin to the muscle or to the muscle group which initiates the pain sensation.

The amount of the neurotoxin administered according to a method within the scope of the disclosed invention can vary according to the particular characteristics of the pain being treated, including its severity and other various patient variables including size, weight, age, and responsiveness to therapy. To guide the practitioner, typically, no less than about 1 unit and no more than about 25 units of a *botulinum* toxin type A (such as BOTOX®) is administered per injection site (i.e. to each muscle portion injected), per patent treatment session. For a *botulinum* toxin type A such as Xeomin®, no less than about 1 unit and no more about 25 units of the *botulinum* toxin type A are administered per injection site, per patent treatment session. For a *botulinum* toxin type A such as DYSPORT®, no less than about 2 units and no more about 125 units of the *botulinum* toxin type A are administered per injection site, per patent treatment session. For a *botulinum* toxin type B such as MYOBLOC®, no less than about 40 units and no more about 1500 units of the *botulinum* toxin type B are administered per injection site, per patent treatment session. Less than about 1, 1, 2 or 40 units (of BOTOX®, Xeomin®, DYSPORT® and MYOBLOC® respectively) can fail to achieve a desired therapeutic effect, while more than about 25, 25, 125 or 1500 units (of BOTOX®), Xeomin®, DYSPORT® and MYOBLOC® respectively) can result in significant muscle hypotonicity, weakness and/or paralysis.

More preferably: for BOTOX® no less than about 2 units and no more about 20 units of a *botulinum* toxin type A; for DYSPORT® no less than about 4 units and no more than about 100 units, and; for MYOBLOC®, no less than about 80 units and no more than about 1000 units are, respectively, administered per injection site, per patent treatment session.

Even more preferably: for BOTOX® no less than about 5 units and no more about 15 units of a *botulinum* toxin type A; for DYSPORT® no less than about 20 units and no more than about 75 units, and; for MYOBLOC®, no less than about 200 units and no more than about 750 units are, respectively, administered per injection site, per patent treatment session. It is important to note that there can be multiple injection sites (i.e. a pattern of injections) for each patient treatment session.

Generally, the total amount of BOTOX®, DYSPORT® or MYOBLOC®, suitable for administration to a patient according to the methods of the invention disclosed herein should not exceed about 300 units, about 1,500 units or about 15,000 units respectively, per treatment session.

The enhancement of therapeutic effect of a neurotoxin for treating the various conditions discussed herein is an improvement of the condition by more than about 5%, preferably more than about 20%, even more preferably more than 50%, as compared to using the same treatment with a neurotoxin but without a wash-down step.

Although examples of routes of administration and dosages are provided, the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14$^{th}$ edition, published by McGraw Hill). For example, the route and dosage for administration of a neurotoxin according to the present disclosed invention can be selected based upon criteria such as the solubility characteristics of the neurotoxin chosen as well as the intensity of pain perceived.

The present invention also includes the use of (a) Clostridial neurotoxins obtained or processed by bacterial culturing, toxin extraction, concentration, preservation, freeze drying, and/or reconstitution; and/or (b) modified or recombinant neurotoxins, that is neurotoxins that have had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made. These neurotoxin variants retain the ability to inhibit neurotransmission between or among neurons, and some of these variants may provide increased durations of inhibitory effects as compared to native neurotoxins, or may provide enhanced binding specificity to the neurons exposed to the neurotoxins. These neurotoxin variants may be selected by screening the variants using conventional assays to identify neurotoxins that have the desired physiological effects of inhibiting neurotransmission.

*Botulinum* toxins for use according to the present invention can be stored in lyophilized, vacuum dried form in containers under vacuum pressure or as stable liquids. Prior to lyophilization the *botulinum* toxin can be combined with pharmaceutically acceptable excipients, stabilizers and/or carriers, such as albumin. The lyophilized material can be reconstituted with saline or water to create a solution or composition containing the *botulinum* toxin to be administered to the patient.

Although the composition may only contain a single type of neurotoxin, such as *botulinum* toxin type A, as the active ingredient to suppress neurotransmission, other therapeutic compositions may include two or more types of neurotoxins, which may provide enhanced therapeutic treatment of a headache. For example, a composition administered to a patient may include *botulinum* toxin type A and *botulinum* toxin type B. Administering a single composition containing two different neurotoxins may permit the effective concentration of each of the neurotoxins to be lower than if a single neurotoxin is administered to the patient while still achieving the desired therapeutic effects. The composition administered to the patient may also contain other pharmaceutically active ingredients, such as, protein receptor or ion channel modulators, in combination with the neurotoxin or neurotoxins. These modulators may contribute to the reduction in neurotransmission between the various neurons. For example, a composition may contain gamma aminobutyric acid (GABA) type A receptor modulators that enhance the inhibitory effects mediated by the $GABA_A$ receptor. The $GABA_A$ receptor inhibits neuronal activity by effectively shunting current flow across the cell membrane. $GABA_A$ receptor modulators may enhance the inhibitory effects of the $GABA_A$ receptor and reduce electrical or chemical signal transmission from the neurons. Examples of $GABA_A$ receptor modulators include benzodiazepines, such as diazepam, oxaxepam, lorazepam, prazepam, alprazolam, halazeapam, chordiazepoxide, and chlorazepate. Compositions may also contain glutamate receptor modulators that decrease the excitatory effects mediated by glutamate receptors. Examples of glutamate receptor modulators include agents that inhibit current flux through AMPA, NMDA, and/or kainate types of glutamate receptors. The compositions may also include agents that modulate dopamine receptors, such as antipsychotics, norepinephrine receptors, and/or serotonin receptors. The compositions may also include agents that affect ion flux through voltage gated calcium channels, potassium channels, and/or sodium channels. Thus, the compositions used to treat pain can include one or more neurotoxins, such as *botulinum* toxins, in addition to ion channel receptor modulators that may reduce neurotransmission.

The neurotoxin may be administered by any suitable method as determined by the attending physician. The methods of administration permit the neurotoxin to be administered locally to a selected target tissue. Methods of administration include injection of a solution or composition containing the neurotoxin, as described above, and include implantation of a controlled release system that controllably releases the neurotoxin to the target tissue. Such controlled release systems reduce the need for repeat injections. Diffusion of biological activity of a *botulinum* toxin within a tissue appears to be a function of dose and can be graduated. Jankovic J., et al *Therapy With Botulinum Toxin*, Marcel Dekker, Inc., (1994), page 150. Thus, diffusion of *botulinum* toxin can be controlled to reduce potentially undesirable side effects that may affect the patient's cognitive abilities. For example, the neurotoxin can be administered so that the neurotoxin primarily effects neural systems believed to be involved in the generation of pain and/or inflammation, and does not have negatively adverse effects on other neural systems.

A polyanhydride polymer, Gliadel® (Stolle R & D, Inc., Cincinnati, OH) a copolymer of poly-carboxyphenoxypropane and sebacic acid in a ratio of 20:80 has been used to make implants, and has been intracranially implanted to treat malignant gliomas. Polymer and BCNU can be co-dissolved in methylene chloride and spray-dried into microspheres. The microspheres can then be pressed into discs 1.4 cm in diameter and 1.0 mm thick by compression molding, packaged in aluminum foil pouches under nitrogen atmosphere and sterilized by 2.2 megaRads of gamma irradiation. The polymer permits release of carmustine over a 2-3 week period, although it can take more than a year for the polymer to be largely degraded. Brem, H., et al, *Placebo-Controlled Trial of Safety and Efficacy of Intraoperative Controlled Delivery by Biodegradable Polymers of Chemotherapy for Recurrent Gliomas*, Lancet 345; 1008-1012:1995.

Implants useful in practicing the methods disclosed herein may be prepared by mixing a desired amount of a stabilized neurotoxin (such as non-reconstituted BOTOX®) into a solution of a suitable polymer dissolved in methylene chloride. The solution may be prepared at room temperature. The solution can then be transferred to a Petri dish and the methylene chloride evaporated in a vacuum desiccator. Depending upon the implant size desired and hence the amount of incorporated neurotoxin, a suitable amount of the dried neurotoxin incorporating implant is compressed at about 8000 p.s.i. for 5 seconds or at 3000 p.s.i. for 17 seconds in a mold to form implant discs encapsulating the neurotoxin. See e.g. Fung L. K. et al., *Pharmacokinetics of Interstitial Delivery of Carmustine 4-Hydroperoxycyclophosphamide and Paclitaxel From a Biodegradable Polymer Implant in the Monkey Brain*, Cancer Research 58;672-684:1998.

Local administration of a *Clostridial* toxin, such as a *botulinum* toxin, can provide a high, local therapeutic level of the toxin. A controlled release polymer capable of long term, local delivery of a *Clostridial* toxin to a target muscle permits effective dosing of a target tissue. A suitable implant, as set forth in U.S. Pat. No. 6,306,423 entitled "Neurotoxin Implant", allows the direct introduction of a chemotherapeutic agent to a target tissue via a controlled release polymer. The implant polymers used are preferably hydrophobic so as to protect the polymer incorporated neurotoxin from water induced decomposition until the toxin is released into the target tissue environment.

The amount of a neurotoxin selected for local administration to a target tissue according to the present disclosed invention can be varied based upon criteria such as the severity of the pain or type of headache being treated, the extent of muscle tissue to be treated, solubility characteristics of the neurotoxin toxin chosen as well as the age, sex, weight and health of the patient. For example, the extent of the area of muscle tissue influenced is believed to be proportional to the volume of neurotoxin injected, while the quantity of the suppressant effect is, for most dose ranges, believed to be proportional to the concentration of a Clostridial toxin administered. Methods for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., $14^{th}$ edition, published by McGraw Hill).

Significantly, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assessed using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality and general health perceptions. Scores obtained can be compared to published values available for various general and patient populations.

EXAMPLES

The following non-limiting example provides those of ordinary skill in the art with specific preferred methods to treat conditions within the scope of the present invention and are not intended to limit the scope of the invention. In the following examples various modes of non-systemic administration of a neurotoxin can be carried out. For example, by intramuscular injection, subcutaneous injection or by implantation of a controlled release implant.

Example 1

Treatment of Headache Pain with Wash-down and Neurotoxin administration

A 46 year old female suffering from near daily headaches and several migraines per month is seen in an outpatient neurology clinic for re-evaluation of her medication. This visit is prompted by a lack of effectiveness of the current medications the patient is taking, which includes topiramate 100 mg, Exedrine, as needed, and frovatriptan for acute attacks.

The patient recently is injected with *botulinum* toxin type A (BoNT/A), but after 2 injection cycles over the previous six months, she reports no relief. To see if she would respond in the absence of topiramate and other medications, the neurologists suggests a novel approach that includes a "wash-down" period (WDP) and "wash-up" period (WUP). The WDP is calculated to be 1.5 weeks, tapering to a dose of 25 mg of topiramate. The patient is instructed not to use acute medications (Exedrin and frovatriptan) 48 hours prior to her visit for BoNT/A injection.

The patient is treated with 150 U of BoNT/A, using the "follow the pain" approach and is instructed to begin the WUP 5 days post-injection and begin tapering up to her previous dose of topiramate (100 mg). One month later, the patient reports a significant decrease in the frequency and intensity of her headaches, with frequency dropping by 80%. The effects of BoNT/A persists for about 4 months, whereupon the patient repeats the previous method and continues to respond.

Example 2

Treatment of Postherpetic Neuralgia with Stepwise Wash-down and Neurotoxin Administration Postherpetic neuralgia is one of the most intractable of chronic pain problems. Patients suffering this excruciatingly painful process often are elderly, have debilitating disease, and are not suitable for major interventional procedures. The diagnosis is readily made by the appearance of the healed lesions of herpes and by the patient's history. The pain is intense and emotionally distressing. Postherpetic neuralgia may occur anywhere, but is most often in the thorax.

A 76 year old man presents a postherpetic type pain, and is on pain medication. The pain is localized to the abdomen region. Prior to the administration of a neurotoxin for the treatment of the pain, the patient is instructed to decrease the intake of the pain medication by 10%. After one week of the taking the pain medication at the reduced dose, the patient is treated by a bolus injection of between about 0.05 U/kg to about 2 U/kg of a neurotoxin intradermally to the abdomen.

Within 7 days, the patient reports a reduction in the level of pain. 60 days after the initial administration of the neurotoxin, the patient is asked to decrease the intake of the pain medication by another 10%. After one week of the taking the pain medication at the reduced dose, the patient is treated by a second bolus injection of between about 0.01 U/kg to about 1 U/kg of a neurotoxin intradermally to the abdomen.

Within 1-7 days after the second administration of the neurotoxin, the patient's pain is even more alleviated. The duration of the pain alleviation is from about 7 to about 27 months.

Example 3

Treatment of Excessive Sweating with Wash-down and Neurotoxin Administration

A male patient, age 65, presents with hyperhidrosis in the hand. The patient is also experiencing pain in the left shoulder, and is taking a pain medication.

Prior to the administration of a neurotoxin for the treatment of the hyperhidrosis, the patient is instructed to decrease the intake of the pain medication by half. After one week of the taking the pain medication at half dose, the patient is treated for the hyperhidrosis, by the administration of 0.05 U/kg to about 2 U/kg of a neurotoxin to the hand. The specific site of administration is to be determined by the physician's knowledge of the anatomy and physiology of the target glands and secretary cells. In addition, the appropriate spinal cord level or brain area can be injected with the toxin. The cessation of excessive sweating after the neurotoxin treatment (in conjunction with a wash-down) is up to 27 months.

Example 4

Treatment of Spasmodic Torticollis with Wash-down and Neurotoxin Administration

A male patient, age 45, presents with a spasmodic torticollis, as manifested by spasmodic or tonic contractions of the neck musculature, producing stereotyped abnormal deviations of the head, the chin being rotated to the side, and the shoulder being elevated toward the side at which the head is rotated. The patient is also taking a prophylactic headache medication.

Prior to the administration of a neurotoxin for the treatment of the spasmodic torticollis, the patient reduces the intake dose of the prophylactic pain medication by 15%. The patient is allowed to take the acute headache medication as needed. After one week of being on the reduced prophylactic headache medication, the patient is administered about 8 U/kg to about 1.5 U/kg of neurotoxins to the appropriate muscles for the treatment of the spasmodic torticollis.

After 3-7 days, the symptoms are substantially alleviated, i.e., the patient is able to hold his head and shoulder in a normal position. The alleviation persists for about 7 months to about 27 months.

Example 5

Treatment of Neuropathic Pain Syndromes with Stepwise Wash-down and Neurotoxin Administration Use of opiates and or other analgesic type pain medications for neuropathic pain conditions such as peripheral diabetic neuropathy, have been used for a number of years.

Prior to the administration of a neurotoxin for the treatment of the pain, the patient is instructed to decrease the intake of the pain medication by 10%. After one week of the taking the pain medication at the reduced dose, the patient is treated by a bolus injection of between about 0.05 U/kg to about 2 U/kg of a neurotoxin via an intramusclar injection to the affected muscles.

Within 7 days, the patient reports a reduction in the level of pain. 60 days after the initial administration of the neurotoxin, the patient is asked to decrease the intake of the pain medication by another 10%. After one week of the taking the pain medication at the reduced dose, the patient is treated by a second bolus injection of between about 0.01 U/kg to about 1 U/kg of a neurotoxin to area or bone pain. Within 1-7 days after the second administration of the neurotoxin, the patient's pain is even more alleviated. The duration of the pain alleviation is from about 7 to about 24 months.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes local administration methods to alleviate a headache pain or to reduce the number of headaches wherein two or more neurotoxins, such as two or more *botulinum* toxins, are administered concurrently or consecutively. For example, *botulinum* toxin type A can be administered until a loss of clinical response or neutralizing antibodies develop, followed by administration of *botulinum* toxin type B. Alternately, a combination of any two or more of the *botulinum* serotypes A-G can be locally administered to control the onset and duration of the desired therapeutic result. Furthermore, non-neurotoxin compounds can be administered prior to, concurrently with or subsequent to administration of the neurotoxin to proved adjunct effect such as enhanced or a more rapid onset of denervation before the neurotoxin, such as a *botulinum* toxin, begins to exert its therapeutic effect.

A method for treating a disorder according to the invention disclosed herein has many benefits and advantages, including the following:

1. Headaches can be eliminated.
2. symptoms of pain, such as a headache pain can be dramatically reduced or eliminated.
3. the symptoms of a pain can be reduced or eliminated for at least about two to about six months per injection of neurotoxin and for from about one year to about five years upon use of a controlled release neurotoxin implant.
4. headaches can be eliminated for at least about two to about six months per injection of neurotoxin and for from about one year to about five years.

Our invention also includes within its scope the use of a neurotoxin, such as a *botulinum* neurotoxin, in the preparation of a medicament for the treatment of a pain, by local administration of the *botulinum* toxin.

All references, articles, patents, applications and publications set forth above are incorporated herein by reference in their entireties. U.S. Pat. Ser. No. 11/039,506 (filed Jan. 18, 2005) is also incorporated in its entirety herein by reference.

Accordingly, the spirit and scope of the following claims should not be limited to the descriptions of the preferred embodiments set forth above.

What is claimed is:

1. A method for alleviating a headache pain for a patient in need thereof, the method comprising the steps of:
    (a) decreasing at least one current dose of a headache medication being used by the patient to a lower dose via a titration process in reverse of a dosing regimen used by the patient to achieve the current dose, the decreasing of the headache medication to a lower dose being a wash-down, and then
    (b) locally administering a therapeutically effective amount of a *botulinum* neurotoxin to the patient subsequent to the wash-down, thereby alleviating the headache pain.

2. The method of claim 1 wherein step (a) occurs within about an amount of time equal to an amount of time that is required to achieve the current dose of a headache medication relative to the lower dose of the headache medication.

3. The method of claim 2 wherein the lower dose is an initial dose or a minimum effective dose (dose at which the patient first reported effectiveness).

4. The method of claim 2 or 3 wherein the amount of time required to achieve the current dose is provided by a product instruction insert of the medication.

5. The method of claim 1 wherein decreasing the current dose is via a titration process.

6. The method of claim 1 wherein decreasing the current dose is via a titration process in reverse of a dosing regimen provided by a product instruction insert of the medication to achieve the current dose.

7. The method of claim 1 wherein step (a) occurs within about an amount of time equal to about 1 to 5 times the half-life of the medication.

8. The method of claim 1 wherein step (a) occurs within about an amount of time equal to 2 times the half-life of the medication.

9. The method of claim 1 wherein step (a) occurs within about an amount of time equal to 2.5 times the half-life of the medication.

10. The method of claim 1 wherein step (a) occurs within about an amount of time equal to 3 times the half-life of the medication.

11. The method of claim 1 wherein step (a) occurs within about an amount of time equal to about 2 hours to 6 weeks.

12. The method of claim 1 wherein the lower dose is an initial dose or a minimum effective dose (dose at which the patient first reported effectiveness) of the medication.

13. The method of claim 1 wherein the lower dose is a minimum effective dose of the medication.

14. The method of claim 1 wherein the lower dose is about 0.10 to 0.90 that of a minimum effective dose.

15. The method of claim 1 wherein the lower dose is about 0.75 that of a minimum effective dose.

16. The method of claim 1 wherein the current headache medication is a prophylactic headache medication.

17. The method of claim 1 wherein the current headache medication is an acute headache medication.

18. The method of claim 1 wherein the current headache medication is acetaminophen.

19. The method of claim 1 wherein the neurotoxin is a *botulinum* toxin selected from the group consisting of *botulinum* toxin types A, B, $C_1$, D, E, F and G.

20. The method of claim 1 wherein the neurotoxin is a *botulinum* toxin type A.

21. The method of claim 1 wherein the *botulinum* neurotoxin is administered in an amount of about 1 unit to about 1,000 units.

22. The method of claim 1 wherein the *botulinum* neurotoxinan is administered in an amount of about 1 unit to about 500 units.

23. The method of claim 1 wherein the headache pain is that of a migraine headache.

24. The method of claim 1 wherein the neurotoxin is administered intramuscularly or subcutaneously.

25. The method of claim 1 wherein the neurotoxin is administered locally to a head muscle, face muscle, an upper neck muscle, or a combination thereof.

26. The method of claim 1 wherein the neurotoxin is administered locally to a frontalis muscle, a glabellar muscle, a masseter muscle, a temporalis muscle, a occipitalis muscle, a trapezius muscle, a semispinali muscle, a splenius muscle, a corrugator muscle, a procerus muscle, or a combination thereof.

27. The method of claim 1 wherein after the administration of the neurotoxin, a frequency of the headache pain decreases by more than about 10% as compared to a frequency prior to step (a).

28. The method of claim 1 wherein after the administration of the neurotoxin, the pain intensity decreases by more than about 10% as compared to an intensity prior to step (a).

29. The method of claim 1 further comprising subsequent to step (b), a step (c) of increasing the lower dose of the headache medication.

30. The method of claim 29 wherein step (c) occurs at about when the neurotoxin begins to alleviate the pain.

31. The method of claim 30 wherein step (c) occurs at about 5 to 14 days after the administration of the neurotoxin.

32. The method of claim 30 wherein increasing the lower dose of the headache medication further decreases the frequency of the headache pain.

33. The method of claim 30 wherein increasing the lower dose of the headache medication further decreases the intensity of the headache pain as compared to after the administration of the neurotoxin.

34. A method for alleviating a headache pain for a patient in need thereof, the method comprising the steps of:
    (a) decreasing at least one current dose of a headache medication being used by the patient to a lower dose via a titration process in reverse of a dosing regimen used by the patient to achieve the current dose, and then (b) locally administering a therapeutically effective amount of a *botulinum* neurotoxin to the patient, wherein steps (a) and (b) are repeated, thereby alleviating the headache pain.

35. A method for alleviating a headache pain in a patient in need thereof, the method comprising:
    (a) decreasing a current dose of a headache medication to a lower dose via a titration process in reverse of a dosing regimen used by the patient to achieve the current dose,
    (b) locally administering a therapeutically effective amount of a *botulinum* neurotoxin to the patient subsequent to said decreasing of dose, and then
    (c) increasing the lower dose of the headache medication, thereby alleviating the headache.

36. A method for treating a neuromuscular disorder, an autonomic nervous system disorder or non-headache pain in a patient in need thereof, the method comprising the steps of:
    (a) decreasing at least one current dose of a headache medication being used by the patient to a lower dose via a titration process in reverse of a dosing regimen used by the patient to achieve the current dose, and then
    (b) locally administering a therapeutically effective amount of a *botulinum* neurotoxin to the patient, thereby treating the neuromuscular disorder, autonomic nervous system disorder or non-headache pain.

* * * * *

UNITED STATES PATENT AND TRADEMARK OFFICE
CERTIFICATE OF CORRECTION

PATENT NO.      : 7,824,694 B2                   Page 1 of 4
APPLICATION NO. : 11/330893
DATED           : November 2, 2010
INVENTOR(S)     : Eric R. First et al.

It is certified that error appears in the above-identified patent and that said Letters Patent is hereby corrected as shown below:

Title Page, Item (56)
On page 2, in column 1, under "Other Publications", line 19, delete "Blumenfled" and insert -- Blumenfeld --, therefor.

Title Page, Item (56)
On page 2, in column 1, under "Other Publications", line 33, delete "Homogenate" and insert -- Homogenate, --, therefor.

Title Page, Item (56)
On page 2, in column 2, under "Other Publications", line 21, delete "endopepdidase" and insert -- endopeptidase --, therefor.

Title Page, Item (56)
On page 2, in column 2, under "Other Publications", line 34, delete "Weigand" and insert -- Wiegand --, therefor.

In column 2, line 12, delete "cite" and insert -- site --, therefor.

In column 2, line 37, delete "II" and insert -- II, --, therefor.

In column 3, line 2, delete "(NSAIDS)," and insert -- (NSAIDs), --, therefor.

In column 3, line 12, delete "NSAIDS" and insert -- NSAIDs --, therefor.

In column 3, line 18, delete "gastrointestinal" and insert -- gastro-intestinal --, therefor.

In column 4, line 34, delete "(eg," and insert -- (e.g., --, therefor.

In column 5, line 47, delete "bihds" and insert -- binds --, therefor.

Signed and Sealed this
Twenty-sixth Day of April, 2011

David J. Kappos
*Director of the United States Patent and Trademark Office*

CERTIFICATE OF CORRECTION (continued)
U.S. Pat. No. 7,824,694 B2

In column 6, line 7, delete "neurotransmilter-containing" and insert -- neurotransmitter-containing --, therefor.

In column 6, lines 43-61,
delete "Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$, has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. Biochem J 1;339 (pt 1):159-65:1999, and Mov Disord, 10(3):376:1995 (pancreatic islet B cells contains at least SNAP-25 and synaptobrevin)."
and insert the same on Col. 6, Line 44 as a new paragraph.

In column 6, line 54, delete "$C_1$," and insert -- $C_1$ --, therefor.

In column 7, line 9, delete "hemaglutinin" and insert -- hemagglutinin --, therefor.

In column 7, line 10, delete "nonhemaglutinin" and insert -- nonhemagglutinin --, therefor.

In column 7, line 17, delete "endopepdidase" and insert -- endopeptidase --, therefor.

In column 7, line 27, delete "Rev_56_:80-99)$_{13}$" and insert -- Rev_56_:80-99). --, therefor.

In column 7, line 35, delete "neurotransmifters" and insert -- neurotransmitters --, therefor.

In column 7, line 43, delete "toxn" and insert -- toxin --, therefor.

In column 7, line 47, delete "nonciceptive" and insert -- nociceptive --, therefor.

In column 7, line 48, delete "Blumenfled" and insert -- Blumenfeld --, therefor.

In column 10, line 24, delete "Marjama-Jyons," and insert -- Marjama-Lyons, --, therefor.

In column 10, line 30, delete "hyperhydrosis." and insert -- hyperhidrosis. --, therefor.

In column 10, line 31, delete "1996; 14(3):507," and insert -- 1996; 114(3):507, --, therefor.

In column 10, line 47, delete "Weigand" and insert -- Wiegand --, therefor.

In column 10, line 48, delete "Nauny-Schmiedeberg's" and insert -- Naunyn-Schmiedeberg's --, therefor.

CERTIFICATE OF CORRECTION (continued)
U.S. Pat. No. 7,824,694 B2

In column 10, line 49, delete "Nauny-Schmiedeberg's" and insert -- Naunyn-Schmiedeberg's --, therefor.

In column 10, line 50, delete "PharmacoL" and insert -- Pharmacol. --, therefor.

In column 11, line 65, delete "idiopathic.toe" and insert -- idiopathic toe --, therefor.

In column 12, line 23, delete "gangliocide" and insert -- ganglioside --, therefor.

In column 12, line 63, delete "norepinephine." and insert -- norepinephrine. --, therefor.

In column 14, line 44, delete "(or.more)" and insert -- (or more) --, therefor.

In column 14, line 51, delete "beratti," and insert -- baratii, --, therefor.

In column 14, line 65, delete "headache.or" and insert -- headache or --, therefor.

In column 15, line 28, delete "comprises," and insert -- comprises --, therefor.

In column 15, line 49, delete "beratti," and insert -- baratii, --, therefor.

In column 16, line 32, delete "0.30,.that" and insert -- 0.30, that --, therefor.

In column 17, lines 46-47, delete "levetiraceltam," and insert -- levetiracetam, --, therefor.

In column 18, line 5, delete "as" and insert -- as a --, therefor.

In column 18, line 6, delete "toxinserotype" and insert -- toxin serotype --, therefor.

In column 18, line 7, delete "(e.g." and insert -- (e.g., --, therefor.

In column 18, line 13, delete "(e.g." and insert -- (e.g., --, therefor.

In column 18, line 46, before "methods" delete "20".

In column 19, line 24, delete "(ie," and insert -- (i.e., --, therefor.

In column 19, line 46, delete "disorder,glandular" and insert -- disorder, glandular --, therefor.

In column 19, line 59, delete "(eg," and insert -- (e.g., --, therefor.

In column 20, line 55, delete "spiridle" and insert -- spindle --, therefor.

In column 21, line 27, delete "BOTOX®)," and insert -- BOTOX®, --, therefor.

CERTIFICATE OF CORRECTION (continued)
U.S. Pat. No. 7,824,694 B2

In column 22, line 23, delete "Iyophilized" and insert -- lyophilized --, therefor.

In column 22, line 52, delete "oxaxepam," and insert -- oxazepam, --, therefor.

In column 22, line 53, delete "halazeapam," and insert -- halazepam, --, therefor.

In column 22, line 53, delete "chordiazepoxide," and insert -- chlordiazepoxide, --, therefor.

In column 24, line 53, delete "Exedrin," and insert -- Excedrin, --, therefor.

In column 24, line 63, delete "(Exedrin" and insert -- (Excedrin --, therefor.

In column 26, line 32, delete "intramusclar" and insert -- intramuscular --, therefor.

In column 28, lines 22-23, in claim 22, delete "neurotoxinan" and insert -- neurotoxin --, therefor.